United States Patent [19]
Ueda et al.

[11] Patent Number: 6,118,010
[45] Date of Patent: Sep. 12, 2000

[54] PROCESS FOR THE PREPARATION OF 1-ALKOXYCARBONYL-3-PHENYLPROPYL DERIVATIVES

[75] Inventors: Yasuyoshi Ueda, Himeji; Akira Matsumoto; Hajime Manabe, both of Takasago, all of Japan

[73] Assignee: Kaneka Corporation, Osaka, Japan

[21] Appl. No.: 09/147,255

[22] PCT Filed: May 8, 1997

[86] PCT No.: PCT/JP97/01543

§ 371 Date: Nov. 10, 1998

§ 102(e) Date: Nov. 10, 1998

[87] PCT Pub. No.: WO97/43246

PCT Pub. Date: Nov. 20, 1997

[30] Foreign Application Priority Data

May 10, 1996 [JP] Japan .................................... 8-116545

[51] Int. Cl.[7] ...................... C07D 207/08; C07C 229/28
[52] U.S. Cl. .............................................. 548/532; 560/39
[58] Field of Search ................................ 560/39; 548/532

[56] References Cited

FOREIGN PATENT DOCUMENTS

| 0 190 687 | 8/1986 | European Pat. Off. ...... C07C 101/34 |
|---|---|---|
| 58-103364 | 6/1983 | Japan . |
| 59-118766 | 7/1984 | Japan . |
| 0 239 062 | 9/1987 | Japan . |
| 3-115254 | 5/1991 | Japan . |
| 6-336495 | 12/1994 | Japan . |

*Primary Examiner*—Samuel Barts
*Assistant Examiner*—Brian J. Davis
*Attorney, Agent, or Firm*—Armstrong, Westerman, Hattori, McLeland & Naughton

[57] ABSTRACT

To produce an 1-alkoxycarbonyl-3-phenylpropyl derivative having little amount of impurities and good quality by a simple, efficient and highly productive process which comprises catalytically reducing an 1-alkoxycarbonyl-3-oxo-3-phenylpropyl derivative. 1-Alkoxycarbonyl-3-phenylpropyl derivative is provided and obtained by catalytic redution being carried out in an alcohol or a solvent containing the alcohol in the presence of a strong acid having a concentration of 0.4 to 0.5 N, the amount of the strong acid being at least 3 equivalents based on one equivalent of the 1-alkoxycarbonyl-3-oxo-3-phenylpropyl derivative (1 mole).

22 Claims, No Drawings

PROCESS FOR THE PREPARATION OF 1-ALKOXYCARBONYL-3-PHENYLPROPYL DERIVATIVES

TECHNICAL FIELD

The present invention relates to a technical field wherein in a process for preparing an 1-alkoxycarbonyl-3-phenylpropyl derivative (hereinafter referred also to as an "1-alkoxycarbonyl-3-phenylpropyl derivative (II)") represented by the formula (II):

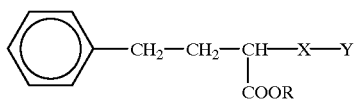
(II)

wherein R is an alkyl group, X is -Ala-, -Gly-, -Leu-, -Ile-, -Val-, -Orn-, -Lys- or -Hly-, in which ω-amino groups of -Orn-, -Lys- and -Hly- are protected with an acyl protecting group, Y is hydroxyl group which comprises catalytically reducing an 1-alkoxycarbonyl-3-oxo-3-phenylpropyl derivative (hereinafter referred also to as an "1-alkoxycarbonyl-3-oxo-3-phenylpropyl derivative (I)") represented by the formula (I):

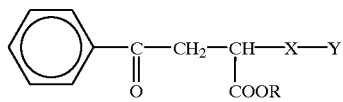
(I)

wherein R, X and Y are the same as the defined above, an 1-alkoxycarbonyl-3-phenylpropyl derivative (II) having little amount of impurities can simply, efficiently and in good productivity be produced and obtained. The 1-alkoxycarbonyl-3-phenylpropyl derivative (II), particularly one having 1S-configuration, is a very useful compound as a drug or an intermediate thereof, particularly various antihypertensive agents such as enalapril and lisinopril, or an intermediate thereof.

BACKGROUND ART

A method of obtaining an 1-alkoxycarbonyl-3-phenylpropyl derivative (II) by catalytically reducing an 1-alkoxycarbonyl-3-oxo-3-phenylpropyl derivative (I) in an alcohol or a solvent containing the alcohol using a transition metal catalyst such as palladium, nickel or platinum as a reduction catalyst is described, for example, in Japanese Examined Patent Publication Nos. 22867/1991 and 4308/1992 and Japanese Unexamined Patent Publication No. 336495/1994.

As the concrete examples of palladium of the reduction catalyst there are, for example, Pd—C, Pd black, and the like. As the concrete examples of nickel there are, for example, Raney Ni, Ni boride, and the like. And as the concrete examples of platinum there are, for example, Pt—C, Pt black, and the like.

For example, Japanese Unexamined Patent Publication No. 336495/1994 discloses an example wherein catalytic reduction is conducted using N-(1-ethoxy-carbonyl-3-oxo-3-phenylpropyl)-L-alanyl-L-proline as a substrate in a water-ethanol mixed solvent (pH 1) containing hydrogen chloride at 20° C. under a pressure of 10 kg/cm² for 35 hours. The gazette discloses that the catalytic reduction is preferably conducted at a pH range from 0.5 to 4, particularly pH 1. Incidentally, a method of separating a product is not disclosed.

Japanese Examined Patent Publication No. 4308/1992 discloses an example wherein catalytic reduction is conducted using $N^2$-(1-ethoxycarbonyl-3-oxo-3-phenylpropyl)-$N^6$-trifluoroacetyl-L-lysine as a substrate in a water-containing ethanol having a hydrogen chloride concentration of about 0.30 N at 40° C. under atmospheric pressure and then $N^2$-(1-ethoxycarbonyl-3-phenylpropyl)-$N^6$-trifluoroacetyl-L-lysine is separated by crystallizing in an aqueous solution, followed by recrystallizing from water-ethanol.

Further, Japanese Examined Patent Publication No. 22867/1991 discloses an example wherein catalytic reduction is conducted using N-(1-ethoxycarbonyl-3-oxo-3-phenylpropyl)-L-alanine ((1S/1R)=95/5) as a substrate in anhydrous ethanol having a sulfuric acid concentration of about 0.38 N at room temperature under atmospheric pressure, and then N-(1-ethoxycarbonyl-3-phenylpropyl)-L-alanine ((1S/1R)=99/1) is separated through extraction with dichloromethane and crystallization from ethyl acetate.

In the above examples, the above catalytic reduction reaction is generally conducted in an alcohol or a solvent containing an alcohol which contains acid such as formic acid, hydrochloric acid, sulfuric acid or phosphoric acid in a low concentration or no acid, using a substrate in a low concentration of about 0.1 mol/L under a pressure within a range from atmospheric pressure to, for example, at most 50 kg/cm².

It is considered that the above catalytic reduction reaction gently proceeds in good yield in a hydrogenation process of the following steps:

First step: carbonyl group binding directly to benzene ring is hydrogenated to form alcohol form (hydroxyl group); and Second step: the alcohol form (hydroxyl group) is further hydrogenated to form methylene group.

However, the present inventors have found that the above catalytic reduction reaction has the following problems as a result of their examination.

That is,

①  the reaction of the first step proceeds in comparatively good manner in the above catalytic reduction reaction but the reaction of the second step is considerably slower than that of the first step (the second step is a rate-determining step, and the time required for the reaction largely depends on the reaction time of the second step).

②  During the catalytic reduction reaction, a side reaction (formation of cyclohexane ring due to the hydrogenation of benzene ring) proceeds to form an 1-alkoxycarbonyl-3-cyclohexylpropyl derivative (hereinafter referred also to as an "1-alkoxycarbonyl-3-cyclohexylpropyl derivative (III)" or a "cyclohexyl form (III)") represented by the formula (III):

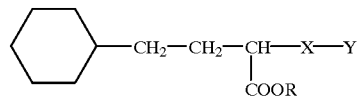
(III)

wherein R, X and Y are the same as the defined above as a by-product, thereby exerting a severe bad influence on quality of the desired compound. Further, it is very difficult to remove the cyclohexylpropyl derivative.

③ When the amount of a catalyst is reduced or the activity thereof is reduced so as to control formation of the above 1-alkoxycarbonyl-3-cyclohexylpropyl derivative (cyclohexyl form) (III) as a by-product, another side reaction (conversion of the alkoxycarbonyl group into carboxyl group) proceeds to form a 1-carboxy-3-phenylpropyl derivative (hereinafter referred also to as a "1-carboxy-3-phenylpropyl derivative (IV)" or a "carboxy form (IV)") represented by the general formula (IV):

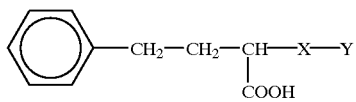

(IV)

wherein X and Y are the same as the defined above as a by-product. As a result, a severe problem such as that a yield of the desired compound is reduced arises.

④ The bad influence on the quality and the yield of the desired compound is liable to be further increased in higher substrate concentration.

As a result of the present inventor's study, it has become apparent that formation of the above 1-carboxy-3-phenylpropyl derivative (carboxy form) (IV) as a by-product is caused by hydrogenation of a lactone form which is formed by cyclization of an intermediate (alcohol form) as shown in the following reaction formula:

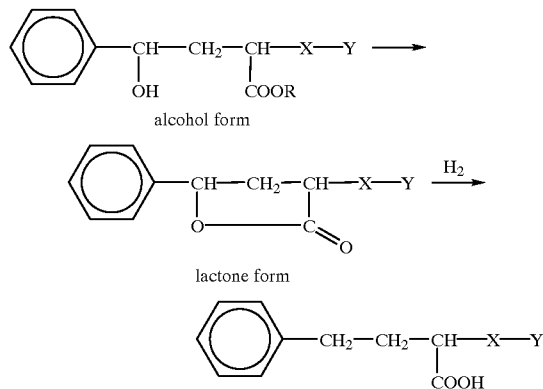

wherein R, X and Y are the same as the defined above.

The formation of impurities such as the above cyclohexyl form (III) and carboxy form (IV) exerts a bad influence on the quality and yield. Inclusion of those impurities into the product should be avoided to the utmost. Particularly, it has been found that the above cyclohexyl form (III) is a similar compound to the 1-alkoxycarbonyl-3-phenylpropyl derivative (II) in structure and that the cyclohexyl form is an impurity whose removal is very difficult.

In order to remove those impurities, other steps having excellent removal effect are required. Those steps cause use of a large amount of an unfavorable organic solvent, complication of the steps (for example, extraction and crystallization using the organic solvent, elimination of the solvent), consumption of time for the above, increase in number of (expensive) apparatuses and volume thereof, reduction in yield, and the like.

The aforementioned Japanese Examined Patent Publication Nos. 22867/1991 and 4308/1992 and Japanese Unexamined Patent Publication No. 336495/1994 do not disclose the formation of the above cyclohexyl form (III) and carboxy form (IV) as by-products in the catalytic reduction reaction, and other steps for simple and effective removal are not disclosed in the publications.

Japanese Examined Patent Publication No. 22867/1991 discloses some steps wherein N-(1-ethoxycarbonyl-3-oxo-3-phenylpropyl)-L-alanine ((1S/1R)=95/5) is catalytically reduced, and then N-(1-ethoxycarbonyl-3-phenylpropyl)-L-alanine ((1S/1R)=99/1) is isolated through extraction with dichloromethane and crystallization from ethyl acetate. However the steps are insufficient in effect of removing impurities, and have several disadvantages such as use of a large amount of an unfavorable organic solvent, complication of the steps (for example, extraction and crystallization using the organic solvent, elimination of the solvent), consumption of time for the above, increase in number of (expensive) apparatuses and volume thereof.

Therefore, in the production of an 1-alkoxycarbonyl-3-phenylpropyl derivative such as the production of $N^2$-(1-ethoxycarbonyl-3-phenylpropyl)-$N^6$-trifluoroacetyl-L-lysine by catalytic reduction of $N^2$-(1-(1-ethoxycarbonyl-3-oxo-3-phenylpropyl)-$N^6$-trifluoroacetyl-L-lysine, the production of N-(1-ethoxycarbonyl-3-phenylpropyl)-L-alanine by catalytic reduction of N-(1-ethoxycarbonyl-3-oxo-3-phenylpropyl)-L-alanine or the production of the 1-alkoxycarbonyl-3-phenylpropyl derivative (II) by catalytic reduction of the 1-alkoxycarbonyl-3-oxo-3-phenylpropyl derivative (I), it is very important to develop a process for preparing the 1-alkoxycarbonyl-3-phenylpropyl derivative (II) having good quality, which contains little amount of impurities such as the 1-alkoxycarbonyl-3-cyclohexylpropyl derivative (cyclohexyl form) (III) and the 1-carboxy-3-phenylpropyl derivative (carboxy form) (IV), simply, efficiently and in good productivity.

An object of the present invention is to provide a very simple, efficient and highly productive process for preparing the 1-alkoxycarbonyl-3-phenylpropyl derivative (II) having good quality by catalytic reduction of the 1-alkoxycarbonyl-3-oxo-3-phenylpropyl derivative (I) wherein content of impurities such as the 1-alkoxy-carbonyl-3-cyclohexylpropyl derivative (cyclohexyl form) (III) and the 1-carboxy-3-phenylpropyl derivative (carboxy form) (IV) is little.

Another object of the invention is to provide a very simple, efficient and highly productive process for preparing N-(1(S)-ethoxycarbonyl-3-phenylpropyl)-L-alanine having good quality, wherein contamination of impurities is little, from N-(1-ethoxycarbonyl-3-phenylpropyl)-L-alanine which is obtained by catalytic reduction of N-(1-ethoxycarbonyl-3-oxo-3-phenylpropyl)-L-alanine.

DISCLOSURE OF THE INVENTION

The present inventors have intensively studied about a process for preparing the 1-alkoxycarbonyl-3-phenylpropyl derivative (II) by catalytic reduction of the 1-alkoxycarbonyl-3-oxo-3-phenylpropyl derivative (I). As a result, it has been found that formation of the 1-alkoxycarbonyl-3-cyclohexylpropyl derivative (cyclohexyl form) (III) as a by-product can be efficiently controlled by carrying out the catalytic reduction reaction under a specific strong acidic condition. Also, it has been found that after the completion of the reaction, the 1-carboxy-3-phenylpropyl derivative (carboxy form) (IV)

formed as a by-product can be effectively removed by separating the 1-alkoxycarbonyl-3-phenylpropyl derivative (II) in the presence of water. It has further been found that, in order to obtain N-(1(S)-ethoxycarbonyl-3-phenylpropyl)-L-alanine having good quality by removing N-(1-carboxy-3-phenylpropyl)-L-alanine formed as a by-product and coexistent N-(1(R)-ethoxycarbonyl-3-phenylpropyl)-L-alanine from N-(1-ethoxycarbonyl-3-phenylpropyl)-L-alanine obtained by the catalytic reduction of N-(1-ethoxycarbonyl-3-oxo-3-phenylpropyl)-L-alanine, it is extremely effective to crystallize in an aqueous solution.

The present invention is made on the basis of the new knowledge as shown above and relates to in a process for preparing an 1-alkoxycarbonyl-3-phenylpropyl derivative represented by the formula (II):

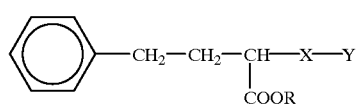

(II)

wherein R is an alkyl group, X is -Ala-, -Gly-, -Leu-, -Ile-, -Val-, -Orn-, -Lys- or -Hly-, in which ω-amino groups of -Orn-, -Lys- and -Hly- are protected with an acyl protecting group, Y is hydroxyl group which comprises catalytically reducing an 1-alkoxycarbonyl-3-oxo-3-phenylpropyl derivative represented by the formula (I):

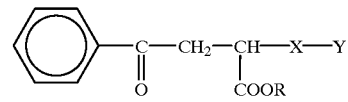

(I)

wherein R, X and Y are the same as the defined above; the above-mentioned catalytic reduction being carried out in an alcohol or a solvent containing the alcohol in the presence of a strong acid having a concentration of 0.4 to 5 N, the amount of the strong acid being at least 3 equivalents based on one equivalent of the 1-alkoxycarbonyl-3-oxo-3-phenylpropyl derivative (1 mole) to control a formation of an 1-alkoxycarbonyl-3-cyclohexylpropyl derivative represented by the formula (III):

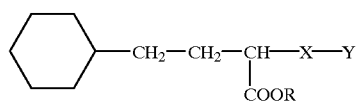

(III)

wherein R, X and Y are the same as the defined above (Claim 1);

a process as claimed in Claim 1 wherein in separating the 1-alkoxycarbonyl-3-phenylpropyl derivative represented by the formula (II) from a reaction solution obtained by catalytic reduction, by crystallization or extraction of the derivative represented by the formula (II), a 1-carboxy-3-phenylpropyl derivative represented by the formula (IV):

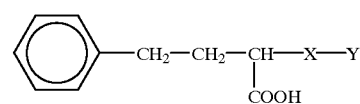

(IV)

wherein X and Y are the same as the defined above as a by-product, is removed to separate the 1-alkoxycarbonyl-3-phenylpropyl derivative represented by the formula (II) (Claim 2);

a process as claimed in Claim 2 wherein the strong acid is neutralized to pH 4.6±1.5 (Claim 3);

a process as claimed in Claim 1, 2 or 3 wherein X is -L-Ala- (Claim 5);

a process as claimed in Claim 1, 2 or 3 wherein X is -L-Lys-, ω-amino group of which is protected with an acyl protecting group (Claim 6);

a process as claimed in Claim 5 or 6 wherein the separation of the 1-alkoxycarbonyl-3-phenylpropyl derivative represented by the formula (II) is carried out by crystallization from the aqueous solution (Claim 7);

a process as claimed in Claim 7 wherein crystallization is carried out at temperatures not less than 30° C. (Claim 8);

a process as claimed in Claim 1, 2, 3, 5, 6, 7 or 8 wherein a Michael addition reaction mixture which contains the 1-alkoxycarbonyl-3-oxo-3-phenylpropyl derivative represented by the formula (I) obtained by Michael addition reaction of a β-benzoyl acrylate and an amino acid or a derivative thereof is used for catalytic reduction (Claim 9);

a process as claimed in Claim 1, 2, 3, 5, 6, 7, 8 or 9 wherein an alcohol, a water content of which is at most 50% (w/w), is used as a reaction solvent (Claim 10);

a process as claimed in Claim 10 wherein an alcohol, a water content of which is within a range from 2 to 30% (w/w), is used as a reaction solvent (Claim 11);

a process as claimed in Claim 1, 2, 3, 5, 6, 7, 8, 9, 10 or 11 wherein sulfuric acid is used as a strong acid (Claim 12);

a process as claimed in Claim 1, 2, 3, 5, 6, 7, 8, 9, 10, 11 or 12 wherein said strong acid is used in a concentration within a range from 3 to 15 equivalents based on 1 mole of the 1-alkoxycarbonyl-3-oxo-3-phenylpropyl derivative represented by the formula (I) as a 1 equivalent (Claim 13);

a process as claimed in Claim 1, 2, 3, 5, 6, 7, 8, 9, 10, 11, 12 or 13 wherein a palladium catalyst is used as a reduction catalyst (Claim 14);

a process as claimed in Claim 14 wherein Pd—C, Pd—alumina or Pd—zeolite is used as a reduction catalyst (Claim 15);

a process as claimed in Claim 1, 2, 3, 5, 6, 7, 8, 9, 10, 11, 12, 13, 14 or 15 wherein a reaction temperature of catalytic reduction is within a range from 10° to 35° C. (Claim 16);

a process as claimed in Claim 1, 2, 3, 5, 6, 7, 8, 9, 10, 11, 12, 13, 14, 15 or 16 wherein a pressure of hydrogen in said catalytic reduction is within a range from atmospheric pressure to 2 kg/cm²G (Claim 17);

a process as claimed in Claim 1, 2, 3, 5, 6, 7, 8, 9, 10, 11, 12, 13, 14, 15, 16 or 17 wherein said catalytic reduction reaction is stopped before an intermediate represented by the formula:

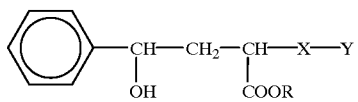

wherein R, X and Y are the same as the defined above disappears (Claim 18);

- a process for obtaining an N-(1(S)-ethoxycarbonyl-3-phenylpropyl)-L-alanine which is characterized by crystallizing N-(1(S)-ethoxycarbonyl-3-phenylpropyl)-L-alanine in the presence of at least one of N-(1-carboxy-3-phenylpropyl)-L-alanine and (N-(1(R)-ethoxycarbonyl-3-phenylpropyl)-L-alanine in an aqueous solution to give N-(1(S)-ethoxycarbonyl-3-phenylpropyl)-L-alanine and to remove N-(1-carboxy-3-phenylpropyl)-L-alanine and (N-(1(R)-ethoxycarbonyl-3-phenylpropyl)-L-alanine (Claim 20); and
- a process as claimed in Claim 20 wherein a pH value of said aqueous solution is pH 4.6±1.5 (Claim 21).

BEST MODE FOR CARRYING OUT THE INVENTION

A process for preparing the 1-alkoxycarbonyl-3-phenylpropyl derivative represented by the formula (II) by catalytically reducing the 1-alkoxycarbonyl-3-oxo-3-phenylpropyl derivative represented by the formula (I) in the present invention will be explained.

In the present invention, the 1-alkoxycarbonyl-3-phenylpropyl derivative represented by the formula (II) is produced by catalytically reducing the 1-alkoxycarbonyl-3-oxo-3-phenylpropyl derivative represented by the formula (I) in an alcohol or a solvent containing the alcohol in the presence of a strong acid having a concentration of 0.4 to 5 N, the amount of the strong acid being at least 3 equivalents based on one equivalent of the 1-alkoxycarbonyl-3-oxo-3-phenylpropyl derivative represented by the formula (I) (1 mole).

In the 1-alkoxycarbonyl-3-oxo-3-phenylpropyl derivative represented by the formula (I):

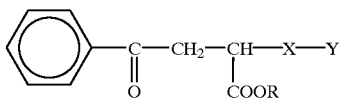
(I)

which is a substrate used in the present invention, R is an alkyl group. Usually an alkyl group having 1 to 8 carbon atoms, preferably a normal chain or branched chain alkyl group having 1 to 4 carbon atoms are preferable in view of easiness of preparing the above substrate or easiness of eliminating in case of hydrolysis. As the concrete examples thereof there can be employed, for instance, methyl group, ethyl group, and the like. Among them, ethyl group is preferable because it can be commonly used as various antihypertensive agents such as enalapril or an intermediate thereof.

As the X in the formula (I) there can be employed, -Ala-, -Gly-, -Leu-, -Ile-, -Val-, -Orn-, -Lys- or -Hly-, in which ω-amino group of -Orn-, -Lys- and -Hly- are protected with an acyl protecting group. They mean an amino acid residue wherein each one of hydrogen atom and hydroxy group is removed from amino group and carboxyl group, respectively of alanine, glycine, leucine, isoleucine, valine, ornithine, lysine or homolysine in which ω-amino group of ornithine, lysine and homolysine are protected with an acyl protecting group.

As the Y in the formula (I) there can be employed, hydroxy group, -Ala, -Gly, -Leu, -Ile, -Val, -Pro, a group represented by the formula:

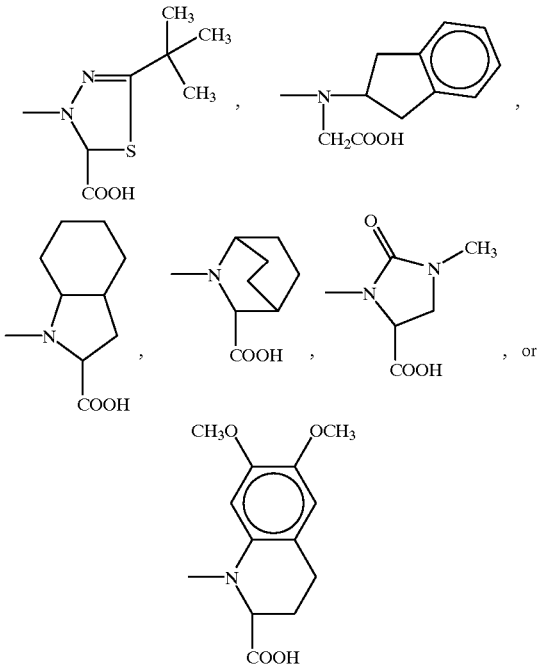

The above-mentioned -Ala, -Gly, -Leu, -Ile, -Val and -Pro mean an amino acid residue wherein one of hydrogen atom is removed from amino group of alanine, glycine, leucine, isoleucine, valine and proline, respectively.

The above X may be taken together with Y to form one group, and as the group formed by that X is taken together with Y there can be employed a group represented by the formula:

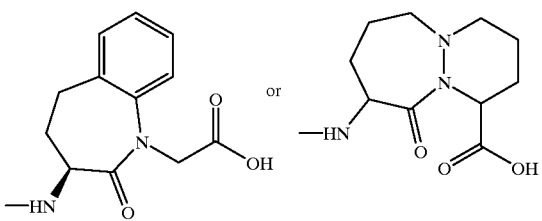

As the protecting group X of ω-amino group of -Orn-, -Lys-, -Hly-, or the like, there can be preferably employed an acyl protecting group such as trifluoroacetyl group, formyl group or phthaloyl group because the acyl protecting group is not easily eliminated at the time of the catalytic reduction and does not show nucleophilic property similar to other neutral amino acid group and, furthermore, influence thereof on the concentration and equivalent of the strong acid to be added at the time of the catalytic reduction is small. The trifluoroacetyl group is particularly preferred.

As the combination of X and Y, a combination of -Ala- and -Pro, particularly a combination of -L-Ala- and -L-Pro, is useful in a production of enalapril. A combination of -Lys-, ω-amino group of which is protected with an acyl protecting group and -Pro, or -Lys-, ω-amino group of which is protected with an acyl protecting group and hydroxyl group; preferably -L-Lys-, ω-amino group of which is protected with an acyl protecting group and -L-Pro, or -L-Lys-, ω-amino group of which is protected with an acyl protecting group and hydroxyl group; more preferably -L-Lys-, ω-amino group of which is protected with trifluoroacetyl group and -L-Pro, or -L-Lys-, ω-amino group of which is protected with a trifluoroacetyl group and hydroxyl group is useful in the production of lisinopril. Further, a combination of -Ala- and hydroxyl group, preferably -L-Ala- and hydroxyl group, is useful as a common intermediate in the production of various antihypertensive agents such as enalapril.

In the formula (I), the derivative wherein the carbon atom at the 1-position to which an alkoxycarbonyl group is bonded has S-configuration, X is L type (i.e. S-configuration) and Y (other than hydroxyl group) is L type (i.e. S-configuration); or one wherein, when X is taken together with Y to form one group and the carbon atom to which carboxyl group is bonded in the group is asymmetric carbon atom, the carbon atom has S-configuration; is generally useful in the production of an antihypertensive agent or an intermediate thereof (when the other asymmetric carbon atom is present, there can be used those having a desired configuration with respect to the asymmetric carbon atom).

In the present invention, any substrate described above can be preferably used. Particularly, those represented by the formula (I) wherein a combination of -Ala- and -Pro, or -Ala- and hydroxyl group; preferably -L-Ala- and -L-Pro, or -L-Ala- and hydroxyl group; and a combination of -Lys-, ω-amino group of which is protected with an acyl protecting group and -Pro, or -Lys-, ω-amino group of which is protected with an acyl protecting group and hydroxyl group; preferably -L-Lys-, ω-amino group of which is protected with an acyl protecting group and -L-Pro, or -L-Lys-, ω-amino group of which is protected with an acyl protecting group and hydroxyl group; more preferably -L-Lys-, ω-amino group of which is protected with trifluoroacetyl group and -L-Pro, or -L-Lys-, ω-amino group of which is protected with trifluoroacetyl group and hydroxyl group are selected as the combination of X and Y and ethyl group or methyl group is selected as R; becomes preferable 1-alkoxycarbonyl-3-oxo-3-phenylpropyl derivative represented by the formula (I). As the concrete examples thereof there can be employed N-(1-ethoxycarbonyl-3-oxo-3-phenylpropyl)-L-alanine, N-(1-ethoxycarbonyl-3-oxo-3-phenylpropyl)-L-alanyl-L-proline, $N^2$-(1-ethoxycarbonyl-3-oxo-3-phenylpropyl)-$N^6$-trifluoroacetyl-L-lysine and $N^2$-(1-ethoxycarbonyl-3-oxo-3-phenylpropyl)-$N^6$-trifluoroacetyl-L-lysyl-L-proline. Among them, a compound having 1-S-configuration or one having a large amount of a compound having 1S-configuration is particularly preferred.

The above 1-alkoxycarbonyl-3-oxo-3-phenylpropyl derivative (I) can be easily synthesized by subjecting a β-benzoyl acrylate and an amino acid or a derivative thereof, or a β-benzoyl acrylate and a dipeptide or a derivative thereof, to the Michael addition reaction in an alcohol or a solvent containing the alcohol, for instance, as described in Japanese Examined Patent Publication Nos. 22867/1991 and 4308/1992 and Japanese Unexamined Patent Publication No. 336495/1994.

As the example of the above β-benzoyl acrylate there can be employed one wherein ester is formed so that ester group is the above R, the preferred R is the same as the above-mentioned R.

As the β-benzoyl acrylate, two kinds of isomers such as trans form and cis form are present. A trans-β-benzoyl acrylate is preferred in view of easiness of preparing the substrate and improvement in yield of the preferable compound having 1S-configuration.

As the amino acid there can be employed alanine, glycine, leucine, isoleucine or valine. As the derivative of the amino acid there can be employed ornithine, lysine and homolysine, ω-amino groups of which are protected with an acyl protecting group.

As the dipeptide there can be employed those prepared by peptide bond of one of the above amino acids and one of the above Y (except for hydroxyl group). As the derivative of the dipeptide there can be employed those prepared by peptide bond of one of the above derivatives of amino acids and one of the above Y (except for hydroxyl group).

Among the amino acids, derivatives thereof, dipeptides and derivatives thereof, amino acids or derivatives thereof are preferred. Among them, alanine and lysine, ω-amino group of which is protected with an acyl protecting group are more preferred, and -L-alanine-and -L-lysine, ω-amino group of which is protected with an acyl protecting group are particularly preferred.

The solvent used in the Michael addition reaction is an alcohol or a solvent containing the alcohol, as described above. It is preferred to use the alcohol as the solvent because the reaction proceeds rapidly and the yield of the preferable compound having 1S-configuration is high. As the solvent containing the alcohol there can be particularly employed a mixed solvent of an alcohol and water. It is particularly preferred to use the mixed solvent of an alcohol and water in view of improvement in solubility of a base, particularly inorganic base, used in the Michael addition reaction, improvement in charging concentration, improvement in reaction rate and improvement in yield of the compound having 1S-configuration.

As the alcohol as the solvent used in the Michael addition reaction there can be generally employed a normal chain or branched chain monohydric alcohol having 1 to 8 carbon atoms, preferably 1 to 4 carbon atoms. It is preferred to employ an alcohol corresponding to an ester group of the β-benzoyl acrylate so that an ester group of desired compound becomes the same as the ester group even if transesterification is carried out at the time of the Michael addition reaction. The alcohol corresponding to the ester group means, for example, methanol in case of methyl ester, and means ethanol in case of ethyl ester.

When the mixed solvent of the alcohol and water is employed, a water content is at most 50% (w/w), preferably at most 30% (w/w). The water content is preferably within a range from 2 to 30% (w/w), more preferably from 5 to 30% (w/w) in view of improvement in reaction rate, improvement in yield of the preferable compound having 1S-configuration and improvement in reaction yield in case of conducting continuous catalytic reduction.

As the base there can be employed a primary amine, a secondary amine, a tertiary amine, a quaternary ammonium hydroxide, an ion exchange resin using them as an exchange group, an alkali metal hydroxide, an alkali earth metal hydroxide, an alkali metal carbonate, or the like. Among them, a tertiary amine, a quaternary ammonium hydroxide, an alkali metal hydroxide, an alkali metal carbonate are preferred. As the example thereof there can be employed triethylamine, tri-n-propylamine, tetramethylammonium hydroxide, potassium hydroxide, lithium hydroxide, sodium hydroxide, potassium carbonate, lithium carbonate, sodium carbonate, potassium hydrogencarbonate, sodium hydrogencarbonate, or the like, preferably, potassium hydroxide, lithium hydroxide, sodium hydroxide, potassium carbonate, lithium carbonate, sodium carbonate, potassium hydrogencarbonate or sodium hydrogencarbonate, more preferably, a potassium compound such as potassium hydroxide, a lithium compound such as lithium hydroxide.

With respect to the amount of the β-benzoyl acrylate, amino acid or derivative thereof, or dipeptide or derivative thereof and the base to be used, an equivalent ratio of them based on the base is about 1 to 3:1:1, normally about 1:1:1, when 1 mole of each of them corresponds to 1 equivalent.

The reaction temperature is within a range from about −20° to 40° C. It is within a range from about −20° to 20° C., preferably a range from −15° to 10° C., in view of improvement in reaction rate and improvement in yield of the preferable compound having 1S-configuration.

As a reaction process, there can be normally used a process which comprises adding a base over several minutes to 24 hours with stirring so that the base can be sufficiently dispersed into a mixture containing the β-benzoyl acrylate, amino acid or derivative thereof or dipeptide or derivative thereof and solvent, or a process which comprises adding the amino acid or derivative thereof, or dipeptide or derivative thereof and a base or a mixture thereof over several minutes to 24 hours with stirring so that it can be sufficiently dispersed into a mixture containing the β-benzoyl acrylate and solvent.

With respect to the reaction concentration, the concentration of the amino acid or derivative thereof, or the dipeptide or derivative thereof can be within a range from 50 to 1500 mM, preferably a range from 100 to 1000 mM.

As the 1-alkoxycarbonyl-3-oxo-3-phenylpropyl derivative (I), there can be used those prepared from the Michael addition reaction solution by extraction and (or) crystallization. As a simple process, the Michael addition solution can also be continuously used. When it is used continuously, those wherein a formation rate of the 1-alkoxycarbonyl-3-oxo-3-phenylpropyl derivative (I is at least 70% are preferred.

As the X, Y and R in the 1-alkoxycarbonyl-3-phenylpropyl derivative represented by the formula (II):

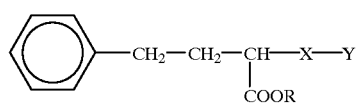

(II)

produced by reducing the 1-alkoxycarbonyl-3-oxo-3-phenylpropyl derivative represented by the formula (I), there can be employed the same as those described in the above 1-alkoxycarbonyl-3-oxo-3-phenylpropyl derivative. It is also similar as to a combination of X and Y.

Accordingly, as the preferable concrete examples of 1-alkoxycarbonyl-3-phenylpropyl derivative represented by the formula (II) there can be employed N-(1-ethoxycarbonyl-3-phenylpropyl)-L-alanine, N-(1-ethoxycarbonyl-3-phenylpropyl)-L-alanyl-L-proline, $N^2$-(1-ethoxycarbonyl-3-phenylpropyl)-$N^6$-trifluoroacetyl-L-lysine and $N^2$-(1-ethoxycarbonyl-3-phenylpropyl)-$N^6$-trifluoroacetyl-L-lysyl-L-proline. Among them, a compound having 1S-configuration thereof or one which has a large amount of a compound having 1S-configuration are particularly preferred.

A reduction catalyst is used in the above catalytic reduction. As the reduction catalyst, there can be used those having preferable catalytic activity and acid resistance, which are prepared by subjecting to an appropriate treatment at the time of preparing the catalyst so as to allow the desired main reaction to proceed preferably under the conditions of the present invention.

As the reduction catalyst, there can be used a reduction catalyst which can be normally used such as a palladium (Pd) catalyst, a nickel catalyst or a platinum catalyst. As the concrete examples of the palladium catalyst, there can be employed, for instance, Pd—C, Pd-alumina, Pd black, Pd—$BaSO_4$, Pd-zeolite, Pd-silicaalumina, and the like. As the concrete examples of the nickel catalyst, there can be employed, for instance, Raney nickel, Ni boride, and the like. As the concrete examples of the platinum catalyst, there can be employed, for instance, Pt—C, Pt black, and the like. Among them, the palladium catalyst is preferred in the synthetic viewpoints of the improvement in reaction rate, improvement in reaction yield and control of by-products (such as an 1-alkoxycarbonyl-3-cyclohexylpropyl derivative represented by the formula (III) and a 1-carboxy-3-phenylpropyl derivative represented by the formula (IV) described hereinafter). Further, Pd—C, Pd-alumina and Pd-zeolite are preferred in view of those described above. Particularly, Pd—C is most preferred. As the examples of the Pd—C, Pd-alumina or Pd-zeolite, there can be employed, for instance, those having a palladium content of 10%, 5%, 2% or 2% (high activity). The reduction catalyst may be used by recycling.

The amount of the reduction catalyst used varies depending on the kind of the catalyst, carrying rate, activity thereof, reaction condition, and the like, and is not specifically limited. In case of the palladium catalyst, it is normally used in an amount of at most 100% (w/w) as a measure based on the substrate in dry basis. In case of Pd—C, it is normally used in an amount of 5 to 50% (w/w) as a measure. Under the strong acidic condition in the present invention, a sufficient reaction rate can be obtained even if a large amount of the reduction catalyst is not used.

As the reaction solvent in the above catalytic reduction reaction, an alcohol or a solvent containing the alcohol is used, as described above. It is preferred to use the alcohol as the solvent in view of the solubility of the substrate and improvement in reaction yield, and the like. As the solvent containing the alcohol there can be employed a mixed solvent of an alcohol and water. It is preferred to employ the mixed solvent of the alcohol and water in view of improvement in reaction yield.

As the alcohol, an alkyl alcohol having the same alkyl group as the above R is generally employed. It is preferred to employ a normal chain or branched chain alcohol having 1 to 8 carbon atoms in view of improvement in solubility of the substrate and improvement in reaction yield. It is more preferred to employ a normal chain or branched chain monohydric alcohol having 1 to 4 carbon atoms in view of low cost, easy handling and easiness of removal in separating the 1-alkoxycarbonyl-3-phenylpropyl derivative (II) after the completion of the reaction. In general, it is preferred to employ an alcohol corresponding to an alkoxyl group of the 1-alkoxycarbonyl-3-oxo-3-phenylpropyl derivative (I) so that even if the alkoxyl group of the derivative (I) is submitted to transesterification with the alcohol, the alkoxyl group is the same as the one prior to transesterification. The alcohol corresponding to the above alkoxyl group is, for example, methanol in case of methoxy group, and is ethanol in case of ethoxy group. In case of ethanol, there can be employed an ethanol containing a denaturant such as toluene or methanol, which is available in low price. For example, ethanol containing toluene as a denaturant may be used.

When the mixed solvent of the alcohol and water is used, the alcohol a water content of which is at most 50% (w/w), preferably at most 30% (w/w) is preferably employed. Among them, the alcohol a water content of which is within a range from 2 to 30% (w/w), more particularly a range from 5 to 30% (w/w) is preferably employed. Depending on the reaction condition, in general when the water content is too higher or lower than the above range, there tend to arise an increase of the amount of impurities such as the 1-alkoxycarbonyl-3-cyclohexylpropyl derivative represented by the formula (III):

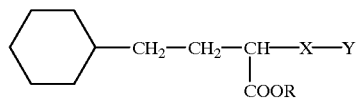
(III)

wherein R, X and Y are the same as the defined above and the 1-carboxy-3-phenylpropyl derivative represented by the formula (IV):

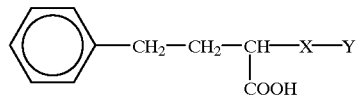
(IV)

wherein X and Y are the same as the defined above.

The above solvent may contain the other solvent as far as a bad influence is not exerted.

The catalytic reduction reaction is normally carried out at a strong acid concentration of a range from 0.4 to 5 N, preferably 0.4 to 4 N, more preferably 0.4 to 3 N, most preferably 0.5 to 3 N. When the strong acid concentration is too lower than the above range, the formation of impurities increases with decrease of the reaction rate. On the other hand, when it is too higher than the above range, the formation rate of the 1-alkoxycarbonyl-3-phenylpropyl derivative (II) decreases.

The term "normality (N)" which represents the concentration of the above strong acid used in the present invention, means the number of gram equivalent of a solute (in this case, strong acid) contained in 1 liter of a solution, similar to the case that "normality (N)" is used for water containing an acid or an alkali. For example, 1 liter of ethanol solution containing 1 mole of sulfuric acid has 2 N concentration and 1 liter of an ethanol solution containing 1 mole of hydrogen chloride has 1 N concentration.

When the strong acid is present in the amount of at least 3 equivalents, normally a range from about 3 to 15 equivalents, preferably from 3 to 12 equivalents, more preferably from 3 to 10 equivalents, based on 1 mole of substrate in case 1 mole of the substrate corresponds to 1 equivalent, it is possible to control the formation of the 1-alkoxycarbonyl-3-cyclohexylpropyl derivative (cyclohexyl form) (III) as a by-product and to maximize the yield of the 1-alkoxycarbonyl-3-phenylpropyl derivative (II).

As the strong acid there can be employed hydrogen chloride, sulfuric acid, and the like. Hydrogen chloride is used as a gas or a solution of hydrochloric acid, preferably hydrochloric acid is employed in view of good easiness of handling. However, sulfuric acid is most preferred in view of control of formation of the 1-alkoxycarbonyl-3-cyclohexylpropyl derivative (cyclohexyl form) (III) as a by-product and improvement in reaction yield of the desired product. Those may be used alone or in combination of 2 or more the strong acids thereof.

Particularly, when a sulfuric acid having 4 to 10 equivalents, preferably 5 to 8 equivalents is employed, in general, stable control of formation of the 1-alkoxycarbonyl-3-cyclohexylpropyl derivative (cyclohexyl form) (III) as a by-product and high yield of the 1-alkoxycarbonyl-3-phenylpropyl derivative (II) can be expected even if other conditions vary more or less.

The presence of the above strong acid contributes to stabilization (control of decomposition) of an unstable substrate, improvement in reaction rate of the catalytic reduction reaction, improvement in solubility of the substrate and product (reduction in the amount of the reaction liquid) and control of impurities, particularly 1-alkoxycarbonyl-3-cyclohexylpropyl derivative (cyclohexyl form) (III) as a by-product.

Since the acidity is too high under the above strong acidic condition, a pH meter can not give a proper indicating value. To carry out the reaction under such a strong acidic condition is very important for realizing control of impurities as by-products, reduction in the amount of the reaction liquid and reduction in reaction time and high yield of the desired product.

Under the above strong acidic condition, it is particularly preferred to employ an alcohol having a water content of 2 to 30% (w/w) as a reaction solvent and to employ sulfuric acid as a strong acid.

With respect to a charging concentration in the reduction reaction, the concentration of the 1-alkoxycarbonyl-3-oxo-phenylpropyl derivative (I) based on the reaction solvent is normally within a range from 0.1 to 1 mol/L, preferably from 0.1 to 0.8 mol/L, more preferably from 0.2 to 0.7 mol/L. When the reaction is carried out within the above concentration range, there can be accomplished advantages of the present invention, such as giving the 1-alkoxycarbonyl-3-phenylpropyl derivative having high quality in good yield and high productivity. Since the optimum strong acid condition slightly varies with the substrate concentration, it is preferred to increase the strong acid concentration and to decrease the amount of the strong acid based on the substrate with increase of the charging concentration.

The reaction temperature in the catalytic reduction reaction is preferably within a range from 0° to 60° C., preferably from 5° to 50° C., more preferably from 10° to 35° C., most preferably from 15° to 30° C. When the reaction temperature is higher than the above range, the amount of the 1-alkoxycarbonyl-3-cyclohexylpropyl derivative (cyclohexyl form) (III) and the 1-carboxy-3-phenylpropyl derivative (carboxy form) (IV) increases. On the other hand, when the reaction temperature is too lower than the above range, the reaction rate is lowered.

The catalytic reduction reaction is preferably carried out at an agitation power of at least 0.2 kW/m$^3$, more preferably at least 0.4 kW/m$^3$, most preferably at least 0.5 kW/m3, so as to avoid decrease in reaction rate and increase in formation of by-products caused by lack of hydrogen supply (contact). The upper limit of the agitation power is not specifically set, and the reaction can be normally carried out at 2 kW/m$^3$ or less without causing a problem.

The above catalytic reduction reaction can be carried out under a range from atmospheric pressure to application of pressure, for example, from atmospheric pressure to 20 kg/cm$^2$G. According to the above strong acid condition in the present invention, a sufficient reaction rate can be obtained when the hydrogen pressure is within a range from about atmospheric pressure to 10 kg/cm²G, preferably from atmospheric pressure to 5 kg/cm²G, more preferably from atmospheric pressure to 2 kg/cm²G and, therefore, a special expensive equipment for reaction applying pressure is not required. To carry out the reaction at low hydrogen pressure furthers control of formation of the 1-alkoxycarbonyl-3-cyclohexylpropyl derivative (cyclohexyl form) (III) as a by-product.

In the catalytic reduction reaction, it is preferred to stop the reaction before the reaction intermediate (alcohol form) represented by the formula:

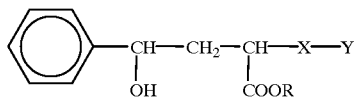

wherein R, X and Y are the same as the defined above disappears. When the reaction is still continued after the reaction intermediate disappeared, the amount of the 1-alkoxycarbonyl-3-cyclohexylpropyl derivative (cyclohexyl form) (III) increases significantly to cause an increase in the amount of by-product. The reaction is stopped when a residual rate of the reaction intermediate is within a range from 1 to 15%, preferably from 2 to 10%. The progress of reaction (consumption of the reaction intermediate) can be known by monitoring the progress of reaction (consumption of the reaction intermediate) using HPLC, GC, and the like. It is also possible to employ a method of stopping the reaction at the time when hydrogen is absorbed in an extent from the amount required to complete the reaction to somewhat less amount. In that case, it is preferred to stop the reaction when about 90% of hydrogen is absorbed.

According to the method for catalytic reduction reaction of the present invention, it is possible to obtain a high-concentration reaction solution of the 1-alkoxycarbonyl-3-phenylpropyl derivative (II) (having a concentration suitable for separation carried out after the completion of the reaction, normally a range from about 0.1 to 1 mol/L) containing a very small amount of the 1-alkoxycarbonyl-3-cyclohexylpropyl derivative (cyclohexyl form) (III) which can not be easily removed by purification, in a short time, without using a large amount of an expensive reduction catalyst and a special expensive equipment for reaction applying pressure.

Next, the process for separating the 1-alkoxycarbonyl-3-phenylpropyl derivative (II) from the reaction solution after the completion of the catalytic reduction reaction will be explained.

After the completion of the reaction, first of all, the reduction catalyst is filtered or separated and the strong acid in the reaction solution is neutralized or removed (when the strong acid is hydrochloric acid, for example, it is also possible to remove it to some degree under reduced pressure). And then, an acid component, which is not favorable (required) in case of separating the 1-alkoxycarbonyl-3-phenylpropyl derivative (II) being present in the reaction solution, is removed to adjust the pH of the reaction solution to a value near an isoelectric point of the 1-alkoxycarbonyl-3-phenylpropyl derivative (II). The isoelectric point of the 1-alkoxycarbonyl-3-phenylpropyl derivative (II) which varies more or less with the kind thereof, is normally within a range of pH 4.6±1.5, preferably pH 4.6±1.0. In case of the pH within the above range, the solubility of the 1-alkoxycarbonyl-3-phenylpropyl derivative (II) in the aqueous solution becomes minimum.

To employ an inorganic base as a base for pH adjustment is preferred because in case of an inorganic base treatment of waste water is easy and a loss of the 1-alkoxycarbonyl-3-phenylpropyl derivative (II) to waste water can be reduced by the salting-out effect. Generally, there can be preferably employed an alkali metal hydroxide, an alkali metal carbonate, alkali metal hydrogencarbonate, and the like. Among them, an alkali metal hydroxide such as sodium hydroxide, potassium hydroxide, lithium hydroxide, or the like is preferred in view of easiness of handling, and sodium hydroxide is most preferred. The base is preferably employed as an aqueous solution such as an aqueous of a range from 2 to 20 N sodium hydroxide solution in view of the operability. Particularly, an aqueous sodium hydroxide solution (9 to 10 N) is preferably employed. The base to be used is not limited thereto, necessarily. Those may be employed alone or in combination thereof.

In order to dissolve salt formed at the time of pH adjustment in the aqueous solution, removal of the alcohol in the reaction solution and addition of water are optionally conducted before or after the pH adjustment. It is preferred to adjust the content of the alcohol in the aqueous solution to a range from about 0 to 20% (w/w), preferably about 0 to 10% (w/w), finally. Normally, it is preferred to carry it out after the pH adjustment in view of stability of the product.

It is generally preferred to adjust the concentration of the above aqueous solution to a value near a saturation concentration of the salt so as to minimize the solubility of the 1-alkoxycarbonyl-3-phenylpropyl derivative (II) by the salting-out effect of the formed salt. However, since the salt formed by neutralization reaction is contained, it is not necessary to add an additional salt, usually.

In the catalytic reduction reaction, the 1-carboxy-3-phenylpropyl derivative (carboxy form) (IV) is normally formed as a by-product in the amount of about 10% (w/w) or less based on the 1-alkoxycarbonyl-3-phenylpropyl derivative (II), although the amount varies depending on the reaction condition. The 1-carboxy-3-phenylpropyl derivative (carboxy form) (IV) can be remained in the aqueous solution, together with the salt formed by the neutralization reaction or pH adjustment, because of comparatively high solubility in the aqueous solution within the above pH range. Therefore, 1-alkoxycarbonyl-3-phenylpropyl derivative (II) can be separated from the 1-carboxy-3-phenylpropyl derivative (carboxy form) (IV) remained in the aqueous solution by crystallizing the 1-alkoxycarbonyl-3-phenylpropyl derivative (II) formed by the catalytic reduction reaction in the aqueous solution or by partitioning or extracting it into the organic solvent from the aqueous solution.

As the method of crystallizing the 1-alkoxycarbonyl-3-phenylpropyl derivative (II) from the aqueous solution there can be employed a concentrating crystallization method after the pH adjustment (including a solvent replacing crystallization method by replacing a solution of the other solvent (such as reaction solution) with water), a cooling crystallization method after the pH adjustment, a neutralizing crystallization method by adjusting the pH to the above pH range, a method of combination thereof, or the like. Among those crystallization methods, the concentrating crystallization method after the pH adjustment is particularly preferably used in view of the operability, quality of the resulting crystal, filtering property, drying property, and the like.

As the method of extracting the 1-alkoxycarbonyl-3-phenylpropyl derivative (II) from the aqueous solution there can be employed batch-wise extraction method, continuous extraction method, and the like.

As the organic solvent used for extraction there can be employed, for instance, a halogenated hydrocarbon, an acetate, an ether, a ketone, and the like. If necessary, the other organic solvent such as toluene can be used in combination.

As the halogenated hydrocarbon there can be employed, for instance, methylene chloride, chloroform, and the like. As the acetate, for example, a normal chain or branched chain alkyl ester having 1 to 5 carbon atoms is preferred in view of improvement in solubility of the 1-alkoxycarbonyl-3-phenylpropyl derivative (II). Particularly, ethyl acetate is most preferred. That is, ethyl acetate is a general-purpose solvent and is easily handled and, further, it is easily removed because of its comparatively low boiling point. As the ether, for example, tetrahydrofuran, methyl-t-butyl ether, or the like is preferred. As the ketone, for example, methyl ethyl ketone, methyl isobutyl ketone, acetone or the like is preferred. Among them, methylene chloride, ethyl acetate, a mixed solvent of methylene chloride and toluene or a mixed solvent of ethyl acetate and toluene is preferred in view of good extraction efficiency, easiness of removal and easiness of handling.

In case of separation, impurities may be removed by extracting impurities after previously adjusting the pH of the aqueous solution to the pH range other than the above pH range, for example, a pH range less than 3.1 or more than 6.1, or the organic layer after extracting may be washed with water within the above pH range, prior to crystallizing or extracting 1-alkoxycarbonyl-3-phenylpropyl derivative (II) for the purpose of avoiding inclusion of impurities at the time of crystallizing or extracting 1-alkoxycarbonyl-3-phenylpropyl derivative (II).

When the 1-alkoxycarbonyl-3-phenylpropyl derivative (II) is an amino acid derivative (Y is hydroxyl group in the above formula (II)), it is liable to be crystallized from the aqueous solution and, therefore, a separation method by means of the above crystallization method is preferably used. Particularly, the concentrating crystallization method (including a solvent replacing crystallization method by replacing a solution of the other solvent (such as reaction solution) with water) after the pH adjustment is preferably employed. When the 1-alkoxycarbonyl-3-phenylpropyl derivative (II) is a dipeptide derivative (Y is a substituent other than hydroxyl group in the above formula (II)), it tends to be difficult to be crystallized from the aqueous solution and, therefore, a separation method by means of the above extraction method is preferably employed.

The separating operation is carried out at a temperature of at most 100° C., normally a range from 5° to 90° C., preferably from 10° to 80° C.

When the 1-alkoxycarbonyl-3-phenylpropyl derivative (II) is an amino acid derivative (Y is hydroxyl group in the above formula (II)), the crystallization is conducted at a temperature of not less than 30° C. in a good manner, preferably at a high temperature of a range from 40° to 70° C. The crystallization at a high temperature within the above range contributes to giving a crystal having high purity and good separation property.

When the 1-alkoxycarbonyl-3-phenylpropyl derivative (II) is a dipeptide derivative (Y is a substituent other than hydroxyl group in the above formula (II)), the crystallization is conducted at a temperature of not more than 60° C., preferably not more than 50° C., more preferably not more than 40° C., normally a range from 0° to 20° C.

The aqueous solution in the separating process of the present invention means an aqueous solution essentially containing water as a solvent (the content of water in the solvent is at least 70%, preferably at least 80%, more preferably at least 90%). For example, it may contain a small amount of the other solvent such as alcohol (for example, ethanol used in the reaction) as far as a bad influence is not exerted.

After the above crystallizing operation, the resulting crystal is separated and washed by a known method such as centrifugal separation, pressure filtration, filtration under reduced pressure. After the above extracting operation, the extraction solution is concentrated under atmospheric pressure or reduced pressure by a known method to give the 1-alkoxycarbonyl-3-phenylpropyl derivative (II).

Thus, the 1-alkoxycarbonyl-3-phenylpropyl derivative (II) can be obtained in high yield in a range from 70 to 90%.

According to the present invention, formation of the 1-alkoxycarbonyl-3-cyclohexylpropyl derivative (cyclohexyl form) (III) as a by-product at the time of the catalytic reduction is controlled and, at the same time, the 1-carboxy-3-phenylpropyl derivative (carboxy form) (IV) formed as a by-product is effectively removed into the aqueous solution. On the other hand, the desired 1-alkoxycarbonyl-3-phenylpropyl derivative (II) can be obtained in high yield from the aqueous salt solution formed by neutralization. Another step for removing the 1-alkoxycarbonyl-3-cyclohexylpropyl derivative (cyclohexyl form) (III) and 1-carboxy-3-phenylpropyl derivative (carboxy form) (IV) by purification is not normally required, but the purification may be conducted so as to give a product having higher purity.

As the preferable 1-alkoxycarbonyl-3-oxo- phenylpropyl derivative (I), to which the above method of the present invention is applied, there can be employed those wherein the combination of X and Y is -L-Ala- and hydroxyl group, or -L-Lys-, ω-amino group of which is protected with an acyl protecting group and hydroxyl group. In that case, in order to separate the 1-alkoxycarbonyl-3-phenylpropyl derivative (II) wherein the combination of X and Y is -L-Ala- and hydroxyl group, or -L-Lys-, ω-amino group of which is protected with an acyl protecting group and hydroxyl group, a process for crystallizing it from the aqueous solution and separating the resulting crystal as described above is preferably used. In that case, there can be obtained several advantages such as that a large amount of the crystal is obtained from the aqueous salt solution formed by neutralization, that the step is simple, that an organic solvent is not additionally used, and that the 1-carboxy-3-phenylpropyl derivative (carboxy form) (IV) can be efficiently removed. It is particularly preferred to separate N-(1-ethoxycarbonyl-3-phenylpropyl)-L-alanine formed by using N-(1-ethoxycarbonyl-3-oxo-phenylpropyl)-L-alanine.

As the method of crystallizing the 1-alkoxycarbonyl-3-phenylpropyl derivative (II) wherein the combination of X and Y is -L-Ala- and hydroxyl group, or -L-Lys-, ω-amino group of which is protected with an acyl protecting group and hydroxyl group from the aqueous solution, there can be employed a concentrating crystallization method (including a solvent replacing crystallization method by replacing a solution of the other solvent (such as reaction solution) with water), after the pH adjustment a cooling crystallization method after the pH adjustment, a neutralizing crystallization method by adjusting the pH to the above pH range, a method of combination thereof, or the like, as described above. Normally, the concentrating crystallization method (including a solvent replacing crystallization method by replacing a solution of the other solvent (such as reaction solution) with water) after the pH adjustment is preferred. In crystallization, impurities may be removed by extracting impurities after previously adjusting the pH of the aqueous solution to the pH range other than the above pH range, for example, a pH range less than 3.1 or more than 6.1, prior to crystallization for the purpose of avoiding inclusion of impurities into the crystal.

The crystallization can be carried out at a temperature of a range from 0° to 100 ° C., normally 5° to 90° C., preferably 10° to 80° C., but it is preferably not less than 30° C., more preferably a range from 40° to 70° C. The crystallization at a high temperature within the above range contributes to giving a crystal having high purity and good separation property. Finally, the yield may be increased by cooling to not more than 25° C., preferably 20° C.

Next, the process of the present invention for obtaining the 1-alkoxycarbonyl-3-phenylpropyl derivative (II) from the 1-alkoxycarbonyl-3-phenylpropyl derivative represented by the formula (II) with which the 1-carboxy-3-phenylpropyl derivative represented by the formula (IV) coexists will be explained.

When the 1-carboxy-3-phenylpropyl derivative (IV) coexists as an impurity with the 1-alkoxycarbonyl-3-phenylpropyl derivative (II), the 1-alkoxycarbonyl-3-phenylpropyl derivative can be obtained by crystallizing or extracting in the presence of water to remove the 1-carboxy-3-phenylpropyl derivative (VI), followed by separating the 1-alkoxycarbonyl-3-phenylpropyl derivative (II).

The above process may be the same as the separating process in the process of the present invention for preparing the 1-alkoxycarbonyl-3-phenylpropyl derivative (II)

The above process is preferably conducted in the presence of water whose pH is adjusted to a value near isoelectric point of the 1-alkoxycarbonyl-3-phenylpropyl derivative (II). The isoelectric point of the 1-alkoxycarbonyl-3-phenylpropyl derivative (II) which varies more or less with the kind thereof, is normally within a range of pH 4.6±1.5, especially pH 4.6±1.0. In case of the pH within the above range, the solubility of the 1-alkoxycarbonyl-3-phenylpropyl derivative (II) in the aqueous solution becomes minimum.

It can also be obtained by dissolving the 1-alkoxycarbonyl-3-phenylpropyl derivative (II) with which the 1-carboxy-3-phenylpropyl derivative (IV) coexists with an acid or an alkali, adjusting the pH of the resulting solution to a value near isoelectric point of the 1-alkoxycarbonyl-3-phenylpropyl derivative (II), followed by recrystallization, or followed by extraction and further recrystallization or partition by replacing the solvent.

The recrystallization and extraction can be conducted by the same crystallizing method or extracting method of the above separating process.

The 1-alkoxycarbonyl-3-phenylpropyl derivative (II) can also be obtained by dissolving the 1-alkoxycarbonyl-3-phenylpropyl derivative (II) with which the 1-carboxy-3-phenylpropyl derivative (IV) coexists in an organic solvent, diluting or replacing the organic solvent with water to remove the 1-carboxy-3-phenylpropyl derivative (IV) into water, and crystallizing.

The 1-alkoxycarbonyl-3-phenylpropyl derivative (II) can also be obtained by dissolving the 1-alkoxycarbonyl-3-phenylpropyl derivative (II) with which the 1-carboxy-3-phenylpropyl derivative (IV) coexists in an organic solvent, washing the resulting solution with water to remove the 1-carboxy-3-phenylpropyl derivative (IV), and crystallizing from the organic layer formed after washing.

According to the above process, the 1-carboxy-3-phenylpropyl derivative (carboxy form) (IV) is efficiently removed in the presence of water and the 1-alkoxycarbonyl-3-phenylpropyl derivative (II) can be obtained in good yield.

When the 1-alkoxycarbonyl-3-phenylpropyl derivative (II) contains the 1-carboxy-3-phenylpropyl derivative (IV) as an impurity, the 1-alkoxycarbonyl-3-phenylpropyl derivative (II) can also be purified so as to further increase the purity of the 1-alkoxycarbonyl-3-phenylpropyl derivative (II) by removing the 1-carboxy-3-phenylpropyl derivative (IV) and separating the 1-alkoxycarbonyl-3-phenylpropyl derivative (II) in the presence of water, using the above process.

Next, the process of the present invention for obtaining N-(1(S)-ethoxycarbonyl-3-phenylpropyl)-L-alanine by crystallization from N-(1(S)-ethoxycarbonyl-3-phenylpropyl)-L-alanine with which at least one of N-(1-carboxy-3-phenylpropyl)-L-alanine and N-(1(R)-ethoxycarbonyl-3-phenylpropyl)-L-alanine coexists will be explained.

By crystallizing N-(1(S)-ethoxycarbonyl-3-phenylpropyl)-L-alanine in an aqueous solution, N-(1-carboxy-3-phenylpropyl)-L-alanine (carboxy derivative), and the like can be effectively removed.

When the desired N-(1(S)-ethoxycarbonyl-3-phenylpropyl)-L-alanine formed by the catalytic reduction using the process of the present invention is separated by the crystallizing method in the above aqueous solution in the process of the present invention, it shows low solubility in an aqueous solution containing the salt formed by the neutralization and is obtained in high crystallization yield. N-(1-carboxy-3-phenylpropyl)-L-alanine formed as a by-product by the catalytic reduction is removed into the aqueous solution.

As the salt mentioned above, sodium sulfate, sodium chloride, and the like are preferred because the amount of N-(1(S)-ethoxycarbonyl-3-phenylpropyl)-L-alanine crystallized is increased by the salting-out effect. In particular, sodium sulfate is preferred.

In the above crystallizing method, the pH is adjusted to a value near isoelectric point of N-(1-ethoxycarbonyl-3-phenylpropyl)-L-alanine. Although the isoelectric point of N-(1-ethoxycarbonyl-3-phenylpropyl)-L-alanine is pH 4.6, it is obtained in high crystallization yield if the pH is adjusted to pH 4.6±1.5, preferably pH 4.6±1.0.

The resulting crystal is separated, washed, and then collected by using a method such as centrifuged separation, pressure filtration, filtration under reduced pressure.

It has been found that, when the reaction solution obtained by the catalytic reduction reaction of the present invention is used with employing N-(1(S)-35 ethoxycarbonyl-3-oxophenylpropyl)-L-alanine with which N-(1(R)-ethoxycarbonyl-3-oxo-3-phenylpropyl)-L-alanine isomer coexists, the N-(1(R)-ethoxycarbonyl-3-phenylpropyl)-L-alanine isomer formed together with N-(1-carboxy-3-phenylpropyl)-L-alanine (carboxy form), can be effectively removed into the aqueous solution by the crystallizing method in the aqueous solution. Incidentally, the reaction intermediate can be easily removed by using the above crystallizing method.

N-(1(S)-ethoxycarbonyl-3-oxo-3-phenylpropyl)-L-alanine with which N-(1(R)-ethoxycarbonyl-3-oxo-3-phenylpropyl)-L-alanine isomer coexists can be easily obtained, for example, by subjecting the ethyl β-benzoyl acrylate and (S)-alanine to the Michael addition reaction in the presence of a base such as an alkali metal hydroxide, an alkali metal carbonate, an alkali metal hydrogencarbonate or an amine as described in Japanese Examined Patent Publication No. 22867/1991 and Japanese Unexamined Patent Publication No. 129260/1987.

When a N-(1-ethoxycarbonyl-3-oxo-3-phenylpropyl)-L-alanine having a large amount of one which has 1S-configuration, preferably containing at most 30% one having 1R-configuration is employed, there can be obtained high quality of N-(1(S)-ethoxycarbonyl-3-phenylpropyl)-L-alanine having a little 1R isomer content.

In crystallization in the above process, the pH is adjusted to a value near isoelectric point of N-(1-ethoxycarbonyl-3-phenylpropyl)-L-alanine, a pH range of 4.6±1.5, preferably pH 4.6±1.0.

By using the process of the present invention of obtaining N-(1(S)-ethoxycarbonyl-3-phenylpropyl)-L-alanine by crystallization, there can be obtained high quality of N-(1(S)-ethoxycarbonyl-3-phenylpropyl)-L-alanine containing a very small amount of N-(1(R)-ethoxycarbonyl-3-phenylpropyl)-L-alanine isomer, simply and efficiently, in good productivity as a crystal even if the catalytic reduction reaction is conducted employing N-(1(S)-ethoxycarbonyl-3-oxo-3-phenylpropyl)-L-alanine with which N-(1(R)-ethoxycarbonyl-3-oxo-3-phenylpropyl)-L-alanine isomer coexists as a substrate.

Preferred basic embodiments of the present invention will be explained hereinafter, however the invention is not limited to the embodiments.

The production of N-(1-ethoxycarbonyl-3-phenylpropyl)-L-alanine from N-(1-ethoxycarbonyl-3-oxo-3-phenylpropyl)-L-alanine will be explained.

N-(1-ethoxycarbonyl-3-oxo-3-phenylpropyl)-L-alanine [(1S/1R)=90/10] (100 g, 0.34 mole) is dissolved in 1100 ml of a 5 to 15% (w/w) water-containing ethanol containing 2 N sulfuric acid (substrate concentration: 0.3 mol/L, amount of sulfuric acid based on substrate: 6 equivalents). Thereto 5% Pd—C (20 g) is added, and immediately after the addition, the obtained mixture is sufficiently mixed and dispersed with supplying a sufficient amount of hydrogen at an agitation power of a 15 range from 0.5 to 1 kW/m$^3$ under the pressure of a range from atmospheric pressure to 0.5 kg/cm$^2$G, and reacted at a range from 20° to 25° C. While the reaction is monitored with HPLC, supply of hydrogen is stopped at the time when hydrogen is absorbed in an extent from 90% of the required amount to somewhat more. Then, the atmosphere is rapidly replaced with an inert gas such as nitrogen gas to stop the reaction. The time required for reaction is at most 10 hours. Pd—C is rapidly removed by filtration and the Pd—C cake is washed with a 5 to 10% (w/w) water-containing ethanol in the amount within a range from the same volume as that of the Pd—C cake to two-fold volume. After 250 ml of water is added to the resulting filtrate, the filtrate was neutralized (pH 4.5) by slowly adding dropwise an aqueous 30% (w/w) sodium hydroxide solution so that an inner temperature does not exceed a range from 20° to 30° C. The filtrate is concentrated at the inner temperature of a range from 50° to 60° C. under reduced pressure, and then concentrated under reduced pressure with appropriately adding water to crystallize slowly with replacing with water. Finally, the ethanol content is at most 2% (w/w), the sodium sulfate content is 10% (w/w) and the pH is 5.0. After cooling to an inner temperature of a range from 20° to 25° C., the resulting crystals are separated with centrifugal separator to eliminate the filtrate sufficiently. The crystals are washed with water in a 2-fold amount of the cake and water is allowed to eliminate sufficiently to obtain N-(1(S)-ethoxycarbonyl-3-phenylpropyl)-L-alanine crystals having good quality (water content: 15 to 20% (w/w) (wet basis) (yield: 75 to 80%). The quality after vacuum drying (40° to 70° C., 30 mmHg to 0.1 mmHg) is as follows: HPLC purity: not less than 99% (w/w), the content of N-(1(R)-ethoxycarbonyl-3-phenylpropyl)-L-alanine: not more than 0.1% (w/w), the content of N-(1-ethoxycarbonyl-3-cyclohexylpropyl)-L-alanine: not more than 0.1% (w/w), the content of N-(1-carboxy-3-phenylpropyl)-L-alanine: not more than 0.1% (w/w), the residue on ignition (residual substance obtained after ashing at a temperature of about 600° C.): not more than 0.1% (w/w).

The production of N$^2$-(1-ethoxycarbonyl-3-phenylpropyl)-N$^6$-trifluoroacetyl-L-lysin from N$^2$-(1-ethoxycarbonyl-3-oxo-3-phenylpropyl)-N$^6$-trifluoroacetyl-L-lysin by using the reaction solution obtained by the Michael addition reaction will be explained hereinafter.

N$^\omega$-trifluoroacetyl-L-lysine (140 g, 0.58 mole) and ethyl trans-β-benzoylacrylate (120 g, 0.59 mole) are added to 1300 ml of a 5 to 10% (w/w) water-containing ethanol. Thereto an aqueous 4 N lithium hydroxide solution (145 ml, 0.58 mole) is added at −10° C. over 5 hours, followed by continuous stirring for 1 hour. As the amount of strong acid in the catalytic reduction in addition to the amount for neutralization of an alkali, 97% (w/w) sulfuric acid (138 g, 1.37 moles) is added with maintaining at the inner temperature of at most 5° C. over 15 minutes. Insoluble matter is removed by filtration and washed with 100 ml of a 5 to 10% (w/w) water-containing ethanol, and then the resulting wash liquid was mixed with the filtrate. To the mixture of the filtrate and wash liquid, 10% Pd—C (42 g) is added. The mixture is sufficiently mixed and dispersed with supplying a sufficient amount of hydrogen at an agitation power of a range from 0.5 to 1 kW/m$^3$ under the pressure of a range from atmospheric pressure to 1 kg/cm$^2$G, and reacted at a range from 25° to 30° C. (substrate concentration: 0.3 mol/L, sulfuric acid concentration: 1.3 N, amount of sulfuric acid based on substrate: 4 equivalents). While the reaction is monitored with HPLC, supply of hydrogen is stopped at the time when hydrogen is absorbed in an extent from 90% of the required amount to somewhat more. Then, the atmosphere is rapidly replaced with an inert gas such as nitrogen gas to stop the reaction. The time required for reaction is at most 10 hours. Pd—C is rapidly removed by filtration and the Pd—C cake is washed with a 5 to 10% (w/w) water-containing ethanol in the amount within a range from the same volume as that of the Pd—C cake to two-fold volume. After 400 ml of water is added to the resulting filtrate, the filtrate was neutralized (pH 5) by slowly adding dropwise an aqueous 30% (w/w) sodium hydroxide solution so that an inner temperature does not exceed a range from 20° to 30° C. The filtrate is concentrated at the inner temperature of a range from 50° to 70° C. under reduced pressure, and then concentrated under reduced pressure with appropriately adding water to crystallize slowly with replacing with water. Finally, the content of ethanol is at most 3% (w/w) and the pH is 5.1. After cooling to an inner temperature of a range from 20° to 30° C., the resulting crystals are separated with centrifugal separator to eliminate the filtrate sufficiently. The crystals are washed with water in a 2-fold amount of the cake and water is allowed to eliminate sufficiently to obtain N$^2$-(1-ethoxycarbonyl-3-phenylpropyl)-N$^6$-trifluoroacetyl-L-lysine crystals having good quality (1S/1R=75 to 85/15 to 25) (water content: 20 to 30% (w/w) (wet basis) (yield: 60 to 70%). The quality after vacuum drying (40° to 70° C., 30 mmHg to 0.1 mmHg) is as follows: HPLC purity: not less than 96% (w/w), the content of N$^2$-(1-ethoxycarbonyl-3-cyclohexylpropyl)-N$^6$-trifluoroacetyl-L-lysine: not more than 0.3% (w/w), the content of N$^2$-(1-carboxy-3-phenylpropyl)-N$^6$-trifluoroacetyl-L-lysine: not more than 0.2% (w/w).

EXAMPLES

The present invention is more specifically described and explained by means of the following Examples, but it is to be understood that the present invention is not limited to the Examples.

The progress of reaction (consumption of reaction intermediate) in catalytic reduction and quantitative determination of the separated product in the Examples of the present invention were conducted basically by using the following HPLC analytical method. The equivalent of the strong acid based on an 1-alkoxycarbonyl-3-oxo-3-phenylpropyl derivative (I) (substrate) means an equivalent of the strong acid when 1 mole of the 1-alkoxycarbonyl-3-oxo-3-phenylpropyl derivative (I) is taken as 1 equivalent.

Production of N-(1-ethoxycarbonyl-3-phenylpropyl)-L-alanine by catalytic reduction of N-(1-ethoxycarbonyl-3-oxo-3-phenylpropyl)-L-alanine.

Quantitative determination of progress of reaction (consumption of reaction intermediate) and product (HPLC).

Column: FINEPAK SIL-C18-5 commercially available from JAPAN SPECTROSCOPIC CO., LTD. 4.6 mmϕ× 250 mm Column temperature: 40° C.

Flow rate: 1.5 ml/min

Detection: UV210 nm

Eluent: 60 mM phosphate buffer (pH 2.5)/acetonitrile= 85/15 (v/v)

Quantitative determination of N-(1-thoxycarbonyl-3-cyclohexylpropyl)-L-alanine (HPLC).

Column: YMC-ODS-A-302 commercially available from YMC CO., LTD. 4.6 mmϕ×150 mm

Column temperature: 25° C.

Flow rate: 1.0 ml/min

Detection: differential refractometer, (RI) Shodex RI-71

Eluent: mixed solution of solution prepared by dissolving 6.8 g of $KH_2PO_4$ in 900 ml of high purity water, adjusting the pH of the resulting solution to 2.5 with 85% (w/w) $H_3PO_4$ aqueous solution, followed by adding high purity water to give 1000 ml of solution, and 1500 ml of methanol Production of $N^2$-(1-ethoxycarbonyl-3-phenyl propyl)-$N^6$-trifluoroacetyl-L-lysine by catalytic reduction of $N^2$-(1-ethoxycarbonyl-3-oxo-3-phenylpropyl)-$N^6$-trifluoroacetyl-L-lysine Quantitative determination of progress of reaction (consumption of reaction intermediate) and product (HPLC).

Column: FINEPAK SIL-C18-5 commercially available from JAPAN SPECTROSCOPIC CO., LTD. 4.6 mmϕ× 250 mm Column temperature: 40° C.

Flow rate: 1.0 ml/min

Detection: Uv210 nm

Eluent: 60 mM phosphate buffer (pH 2.5)/acetonitrile= 65/35 (v/v)

Quantitative determination of $N^2$-(1-ethoxycarbonyl-3-cyclohexylpropyl)-$N^6$-trifluoroacetyl-L-lysine (HPLC).

Column: COSMOSIL 5C-18-AR commercially available from NACALAI TESQUE, INC. 4.6 mmϕ×250 mm Column temperature: 50° C.

Flow rate: 2.0 ml/min

Detection: UV210nm

Eluent: 60mM phosphate buffer (pH 2.5)/acetonitrile=72/ 28 (v/v)

Production of $N^2$-(1-ethoxycarbonyl-3-phenylpropyl)-$N^6$-trifluoroacetyl-L-lysyl-L-proline by catalytic reduction of $N^2$-(1-ethoxycarbonyl-3-oxo-3-phenylpropyl)-$N^6$-trifluoroacetyl-L-lysyl-L-proline.

Quantitative determination of progress of reaction (consumption of reaction intermediate) and product (HPLC).

Column: FINEPAK SIL-C18-5 commercially available from JAPAN SPECTROSCOPIC CO., LTD. 4.6 mmϕ× 250 mm Column temperature: 45° C.

Flow rate: 1.0 ml/min

Detection: UV210 nm

Eluent: 60 mM phosphate buffer (pH 2.5)/acetonitrile= 65/35 (v/v)

Quantitative determination of $N^2$-(1-ethoxycarbonyl-3-cyclohexylpropyl)-$N^6$-trifluoroacetyl-L-lysyl-L-proline (HPLC).

Column: FINEPAK SIL-C18-5 commercially available from JAPAN SPECTROSCOPIC CO., LTD. 4.6 mmϕ× 250 mm Column temperature: 45° C.

Flow rate: 0.8 ml/min

Detection: UV210 nm

Eluent: 60 mM phosphate buffer (pH 2.5)/acetonitrile= 50/50 (v/v)

Example 1

N-(1-ethoxycarbonyl-3-oxo-3-phenylpropyl)-L-alanine [(1S/1R)=9.0] (10.0 g, 34 mmoles) was added to 105 ml of 7% (w/w) water-containing ethanol containing 1.9 N sulfuric acid. Thereto 50% (w/w) water-containing 5% Pd—C (5.0 g) was added and the catalytic reduction was carried out in hydrogen atmosphere (atmospheric pressure) under the conditions of an inner temperature of about 20° C. and an agitation power of a range from 0.5 to 1 kW/m³ (amount of sulfuric acid based on substrate: 6 equivalents). Supply of hydrogen was stopped at the time when hydrogen is absorbed in 90% and somewhat more of the required amount. And then, the atmosphere was rapidly replaced with nitrogen to stop the reaction. Pd—C was rapidly removed by filtration and the Pd—C cake was conscientiously washed with 10 ml of 7% (w/w) water-containing ethanol and 5 ml of water. After 30 ml of water was added to the resulting filtrate, the filtrate was neutralized (pH 4.5) by slowly adding dropwise an aqueous 30% (w/w) sodium hydroxide solution. The filtrate was concentrated at the inner temperature of a range from 40° to 60° C. under reduced pressure, and then concentrated under reduced pressure with appropriately adding water to obtain slurry with replacing with water. The content of ethanol in the slurry was 3% (w/w), the content of sodium sulfate was 9% (w/w) and the pH was 5.0. After cooling to an inner temperature of 20° C., the crystal was filtered and washed with water in a 2-fold amount of the cake. The resulting crystal was vacuum-dried (30 mmHg to 0.1 mmHg) at a range from 40° to 60° C. to obtain N-(1(S)-ethoxycarbonyl-3-phenylpropyl)-L-alanine (6.3 g, 23 mmoles). The yield was 75%. HPLC purity: 99.3% (w/w), the content of N-(1(R)-ethoxycarbonyl-3-phenylpropyl)-L-alanine: not detected, the content of N-(1-ethoxycarbonyl-3-cyclohexylpropyl)-L-alanine: 0.1% (w/w), the content of N-(1-carboxy-3-phenylpropyl)-L-alanine: less than 0.1% (w/w), residue on ignition: 0.1% 35 (w/w).

Example 2

$N^2$-(1-ethoxycarbonyl-3-oxo-3-phenylpropyl)-$N^6$-trifluoroacetyl-L-lysine [(1S/1R)=79/21] (7.0 g, 15.7 mmoles) was added to 100 ml of 10% (w/w) water-containing ethanol containing 0.9 N sulfuric acid. Thereto 50% (w/w) water-containing 5% Pd—C (5.6 g) was added and the catalytic reduction was carried out in hydrogen atmosphere (atmospheric pressure) under the conditions of an inner temperature of about 35° C. and an agitation power of a range from 0.5 to 1 kW/m$^3$ (amount of sulfuric acid based on substrate: 6 equivalents). Supply of hydrogen was stopped at the time when hydrogen is absorbed in 90% and somewhat more of the required amount. And then, the atmosphere was rapidly replaced with nitrogen to stop the reaction. The amount of $N^2$-(1-carboxy-3-phenylpropyl)-$N^6$-trifluoroacetyl-L-lysine as a by-product based on $N^2$-(1-ethoxycarbonyl-3-phenylpropyl)-$N^6$-trifluoroacetyl-L-lysine was 7% (w/w). Pd—C was rapidly removed by filtration and the Pd—C cake was conscientiously washed with 10 ml of 7% (w/w) water-containing ethanol and 5 ml of water. After 100 ml of water was added to the resulting filtrate, the filtrate was neutralized (pH 4.6) by slowly adding dropwise an aqueous 30% (w/w) sodium hydroxide solution. The filtrate was concentrated at the inner temperature of a range from 40° to 60° C. under reduced pressure, and then concentrated under reduced pressure with appropriately adding water to obtain slurry with replacing with water. The content of ethanol in the slurry was 2% (w/w), the content of sodium sulfate was 6% (w/w) and the pH was 5.1. After cooling to an inner temperature of 25° C., the crystal of $N^2$-(1-ethoxycarbonyl-3-phenylpropyl)-$N^6$-trifluoroacetyl-L-lysine was filtered and washed with water in a 2-fold amount of the cake. The resulting crystal was vacuum-dried (30 mmHg to 0.1 mmHg) at a range from 40° to 60° C. to obtain $N^2$-(1-ethoxycarbonyl-3-phenylpropyl)-$N^6$-trifluoroacetyl-L-lysine((1S/1R)=79/2 1) 5.4 g (12.6 mmoles). The yield was 80%. HPLC purity: 98.6% (w/w), the content of $N^2$-(1-ethoxycarbonyl-3-cyclohexylpropyl)-$N^6$-trifluoroacetyl-L-lysine: 0.2% (w/w), the content of $N^2$-(1-carboxy-3-phenylpropyl)-$N^6$-trifluoroacetyl-L-lysine: 0.1% (w/w), residue on ignition: 0.2% (w/w).

Example 3

Using $N^2$-(1-ethoxycarbonyl-3-oxo-3-phenylpropyl)-$N^6$-trifluoroacetyl-L-lysyl-L-proline [(1S/1R)=2] (5.0 g, 9.4 mmoles), the catalytic reduction was conducted in 70 ml of 7% (w/w) water-containing ethanol containing 1.4 N sulfuric acid according to the same manner as that described in Example 1 (amount of sulfuric acid based on substrate: 5 equivalents). Pd—C was removed by filtration and the Pd—C cake was washed with 20 ml of 7% (w/w) water-containing ethanol. Water (10 ml) was added to the resulting filtrate which was neutralized (pH 4.6) by slowly adding dropwise an aqueous 30% (w/w) sodium hydroxide solution. The filtrate was concentrated under reduced pressure at the inner temperature of 20° C. to remove ethanol. After cooling to 10° C., 50 ml of cold water was added, followed by extracting three times with 50 ml of methylene chloride at a range from 5° to 15° C. The resulting methylene chloride layer was washed with 20 ml of cold water at a range from 5° to 15 ° C., and then kept in a freezer for 2 days. After ice is removed, the layer was concentrated under reduced pressure at an inner temperature of at most 20° C. to give a concentrate containing $N^2$-(1-ethoxycarbonyl-3-phenylpropyl)-$N^6$-trifluoroacetyl-L-lysyl-L-proline [(1S/1R)=2]. The yield was 80%. The content of $N^2$-(1-ethoxycarbonyl-3-cyclohexylpropyl)-$N^6$-trifluoroacetyl-L-lysyl-L-proline was 0.2% (w/w) and the content of $N^2$-(1-carboxy-3-phenylpropyl)-$N^6$-trifluoroacetyl-L-lysyl-L-proline was 0.1% (w/w). The resulting concentrate was completely concentrated to dryness and, after dissolving it in 20 ml of methyl t-butyl ether, the solution was concentrated using an evaporator (bath temperature: 20° C.) to reduce the volume to half. A seed crystal of $N^2$-(1(S)-ethoxycarbonyl-3-phenylpropyl)-$N^6$-trifluoroacetyl-L-lysyl-L-proline was added and the solution was crystallized by allowing to stand in a refrigerator. The resulting crystal was rapidly filtered, and then washed with 2 ml of cooled methyl t-butyl ether/ methylcyclohexane (7/3 (v/v)) immediately after filtration. The resulting wet crystal was dissolved in 10 ml of methyl t-butyl ether and the solution was crystallized by allowing to stand in a refrigerator. With vigorously stirring the slurry at 10° C., 3 ml of methylcyclohexane was slowly added. The resulting crystal was rapidly filtered, and then washed with 2 ml of cooled methyl t-butyl ether/methylcyclohexane (7/3 (v/v)) immediately after filtration. The resulting crystal was vacuum-dried (30 mmHg to 1 mmHg) at a range from 20° to 45° C. and mixed with a mixture of 10 ml of water and 0.24 g of sodium carbonate. An aqueous 10% (w/w) sodium hydroxide solution was slowly added at 40° C. to maintain the pH not less than 12.5. Four hours after the addition, the pH was adjusted to 8 with 35% (w/w) hydrochloric acid, 10 ml of methylene chloride was added, and then the pH was adjusted to 5 by adding 35% (w/w) hydrochloric acid. The methylene chloride layer was separated and the aqueous layer was concentrated under reduced pressure by using an evaporator (bath temperature: 45° C.). The aqueous layer was concentrated to reduce the volume to quarter, and then stirred at room temperature for 4 hours to give a thick slurry. The resulting crystal was filtered and washed with 2 ml of water. The resulting wet crystal was vacuum-dried (30 mmHg to 1 mmHg) at 5 0° C. to give $N^2$-(1(S)-carboxy-3-phenylpropyl)-L-lysyl-L-proline dihydrate (lysinoprildihydrate) (0.9 g, 2.1 mmoles). The yield was 33%. HPLC purity: 98% (w/w), the content of a diketopiperazine derivative: less than 0.1% (w/w).

Example 4

N-(1-ethoxycarbonyl-3-oxo-3-phenylpropyl)-L-alanine [(1S/1R)=9.0] 5.0 g, (17 mmoles) was added to 100 ml of 10% (w/w) water-containing ethanol containing 0.5 N HCl. Thereto 50% (w/w) water-containing 5% Pd—C (5.0 g) was added and the catalytic reduction was carried out in hydrogen atmosphere (atmospheric pressure) under the conditions of an inner temperature of a range from about 15° to 25° C. and an agitation power of a range from 0.5 to 1 kW/m$^3$ (amount of HCl based on substrate: 3 equivalents). Supply of hydrogen was stopped at the time when hydrogen is absorbed in 90% of the required amount. Then, the atmosphere was rapidly replaced with nitrogen to stop the reaction. The residual rate of the reaction intermediate was 10%, the formation rate of N-(1-ethoxycarbonyl-3-phenylpropyl)-L-alanine was 82%, the content of N-(1-ethoxycarbonyl-3-cyclohexylpropyl)-L-alanine was 0.2% (w/w) and the content of N-(1-carboxy-3-phenylpropyl)-L-alanine was 7% (w/w). Pd—C was rapidly removed by filtration and the Pd—C cake was conscientiously washed with 10 ml of 7% (w/w) water-containing ethanol and 5 ml of water. After 30 ml of water was added to the resulting filtrate, the filtrate was neutralized (pH 4.5) by slowly adding dropwise an aqueous 30% (w/w) sodium hydroxide solution. The filtrate was concentrated at the inner temperature of 50° C. under reduced pressure, and then concentrated under reduced pressure with appropriately adding water to give a slurry with replacing with water. The content of ethanol in the slurry was 2% (w/w), the content of sodium sulfate was 9% (w/w) and the pH was 5.0. After cooling to an inner temperature of 20° C., the crystal was filtered and washed with water in a 2-fold amount of the cake. The resulting crystal was vacuum-dried (30 mmHg to 1 mmHg) at a range from 40° to 60° C. to give N-(1(S)-ethoxycarbonyl-3-phenylpropyl)-L-alanine (3.1 g, 11 mmoles). The yield was 73%. HPLC purity: 99.1% (w/w), the content of N-(1(R)-ethoxycarbonyl-3-phenylpropyl)-L-alanine: 0.1% (w/w), the content of N-(1-ethoxycarbonyl-3-cyclohexylpropyl)-L-alanine: 0.2% (w/w), the content of N-(1-carboxy-3-phenylpropyl)-L-alanine: 0.1% (w/w).

Example 5

$N^\omega$-trifluoroacetyl-L-lysine (12.1 g, 50 mmoles) and ethyl trans-β-benzoylacrylate (10.2 g, 50 mmoles) were added to 125 ml of 6% (w/w) water-containing ethanol. An aqueous 4 N lithium hydroxide solution (12.5 ml, 50 mmoles) was added at -8° C. over 2 hours, followed by continuous stirring for 30 minutes. The formation rate of $N^2$-(1-ethoxycarbonyl-3-oxo-3-phenylpropyl)-$N^6$-trifluoroacetyl-L-lysine was 90%. As an amount of a strong acid at the time of the catalytic reduction, in addition to a content for neutralization of an alkali, 97 % (w/w) sulfuric acid (17.7 g, 175 mmoles) was added with maintaining at an inner temperature of at most 0° C. over 15 minutes. The insoluble matter was removed by filtration and the filtrate was washed with 125 ml of 6% (w/w) water-containing ethanol, and then the resulting wash liquid was mixed with the filtrate. To the mixture of the filtrate and wash, 50% (w/w) water-containing 5% Pd—C (15 g) was added and the catalytic reduction was carried out in hydrogen atmosphere of a pressure range of atmospheric pressure to 1 kg/cm$^2$G under the conditions of an inner temperature of about 35° C. and an agitation power of 1 kW/m$^3$ (sulfuric acid concentration: 1.1 N, amount of sulfuric acid based on $N^2$-(1-ethoxycarbonyl-3-oxo-3-phenylpropyl)-$N^6$-trifluoroacetyl-L-lysine: 6 equivalents). Supply of hydrogen was stopped at the time when hydrogen is absorbed in 90% of the required amount. Then, the atmosphere was rapidly replaced with nitrogen to stop the reaction. The residual rate of the reaction intermediate was 5%, the formation rate of $N^2$-(1-ethoxycarbonyl-3-phenylpropyl)-$N^6$-trifluoroacetyl-L-lysine ((1S/1R)=79/21) was 80%, the content of $N^2$-(1-ethoxycarbonyl-3-cyclohexylpropyl)-$N^6$-trifluoroacetyl-L-lysine was 0.2% (w/w) and the content of $N^2$-(1-carboxy-3-phenylpropyl)-$N^6$-trifluoroacetyl-L-lysine was 14% (w/w). Pd—C was rapidly removed by filtration and the Pd—C cake was washed with 30 ml of 6% (w/w) water-containing ethanol. After 125 ml of water was added to the resulting filtrate, the filtrate was neutralized (pH 4.6) by slowly adding dropwise an aqueous 30% (w/w) sodium hydroxide solution. The filtrate was concentrated under reduced pressure at the inner temperature of 60° C. to reduce the volume to half, and then 50 ml of water was further added. After cooling to an inner temperature of 25° C., the crystal of $N^2$-(1-ethoxycarbonyl-3-phenylpropyl)-$N^6$-trifluoroacetyl-L-lysine was filtered and washed with water in a 2-fold amount of the cake. The resulting crystal was vacuum-dried (30 mmHg to 1 mmHg) at 60° C. to give $N^2$-(1-ethoxycarbonyl-3-phenylpropyl)-$N^6$-trifluoroacetyl-L-lysine ((1S/1R)=79/21) (13.0 g, 30 mmoles). The yield was 60%. HPLC purity: 97% (w/w), the content of $N^2$-(1-ethoxycarbonyl-3-cyclohexylpropyl)-$N^6$-trifluoroacetyl-L-lysine: 0.2% (w/w), the content of $N^2$-(1-carboxy-3-phenylpropyl)-$N^6$-trifluoroacetyl-L-lysine: 0.1% (w/w).

Example 6

N-(1-ethoxycarbonyl-3-oxo-3-phenylpropyl)-L-alanine [(1S/1R)=9.0] (10.0 g, 34 mmoles) was added to 105 ml of 7% (w/w) water-containing ethanol containing 1.9 N sulfuric acid. Thereto 5% Pd-alumina (2.0 g) was added and the catalytic reduction was carried out in hydrogen atmosphere (atmospheric pressure) under the conditions of an inner temperature of a range from 15° to 25° C. and an agitation power of a range from 0.5 to 1 kW/m$^3$ (amount of sulfuric acid based on substrate: 6 equivalents). Supply of hydrogen was stopped at the time when hydrogen is absorbed in 90% of the required amount. And then, the atmosphere was rapidly replaced with nitrogen to stop the reaction. The formation rate of N-(1-ethoxycarbonyl-3-phenylpropyl)-L-alanine was 80%, the amount of N-(1-ethoxycarbonyl-3-cyclohexylpropyl)-L-alanine(cyclohexyl form) as a by-product based on N-(1-ethoxycarbonyl-3-phenylpropyl)-L-alanine was 0.2% (w/w) and the amount of N-(1-carboxy-3-phenylpropyl)-L-alanine as a by-product was 14% (w/w).

Example 7

N-(1-ethoxycarbonyl-3-oxo-3-phenylpropyl)-L-alanine [(1S/1R)=9.0] (5.0 g, 17 mmoles) was added to 100 ml of toluene-denatured anhydrous ethanol containing 1.0 N sulfuric acid. Thereto 5% Pd—C (1.5 g) was added and the catalytic reduction was carried out in hydrogen atmosphere (atmospheric pressure) under the conditions of an inner temperature of a range from 15° to 25° C. and an agitation power of a range from 0.5 to 1 kW/m$^3$ (amount of sulfuric acid based on substrate: 6 equivalents). Supply of hydrogen was stopped at the time when hydrogen is absorbed in 90% of the required amount. And then, the atmosphere was rapidly replaced with nitrogen to stop the reaction. The formation rate of N-(1-ethoxycarbonyl-3-phenylpropyl)-L-alanine was 80%, the amount of N-(1-ethoxycarbonyl-3-cyclohexylpropyl)-L-alanine (cyclohexyl from) as a by-product based on N-(1-ethoxycarbonyl-3-phenylpropyl)-L-alanine was 0.1% (w/w) and the amount of N-(1-carboxy-3-phenylpropyl)-L-alanine as a by-product was 11% (w/w).

Example 8 and Comparative Example 1

$N^2$-(1-ethoxycarbonyl-3-oxo-3-phenylpropyl)-$N^6$-trifluoroacetyl-L-lysine [(1S/1R)=79/21] (7.0 g, 15.7 mmoles) was added to 100 ml of 30% (w/w) water-containing ethanol containing a predetermined amount of sulfuric acid. The concentration of sulfuric acid and the equivalent thereof based on N-(1-ethoxycarbonyl-3-oxo-3-phenylpropyl)-$N^6$-trifluoroacetyl-L-lysine (substrate) in the solution are shown in Table 1. 5% Pd—C (2.8 g) was added and the catalytic reduction was carried out in hydrogen atmosphere (atmospheric pressure) under the conditions of the inner temperature of 20° C. and an agitation power of 1 kW/m$^3$. While the reaction was monitored with HPLC, the reaction was stopped at the time hen the residual rate of the reaction intermediate was 10%. In Table 1 there are shown the time required for reaction, the formation rate of $N^2$-(1-ethoxycarbonyl-3-phenylpropyl)-$N^6$-trifluoroacetyl-L-lysine, and the amount of $N^2$-(1-ethoxycarbonyl-3-cyclohexylpropyl)-$N^6$-trifluoroacetyl-L-lysine (cyclohexyl form) as a by-product based on $N^2$-(1-ethoxycarbonyl-3-phenylpropyl)-$N^6$-trifluoroacetyl-L-lysine.

TABLE 1

| | Amount of sulfuric acid | | Cyclohexyl form (% (w/w)) | For- mation rate (%) | Time required for reaction (hr) |
|---|---|---|---|---|---|
| | Concentration (N) | Equivalent | | | |
| Ex. 8 | 1.1 | 7 | 0.2 | 83 | about 10 |
| Com. Ex. 1 | 0.3 | 2 | 0.5 | 85 | about at least 30 |

According to the same manner as that described in Example 2, the separation from the resulting reaction solution was conducted. As a result, the effect of removing the cyclohexyl form by purification was not recognized.

Example 9

N-(1-ethoxycarbonyl-3-oxo-3-phenylpropyl)-L-alanine [(1S/1R)=9.0] (10.0 g, 34 mmoles) was added to a mixture of 7% (w/w) water-containing ethanol containing a predetermined amount of sulfuric acid. The concentration of sulfuric acid and the equivalent thereof based on N-(1-ethoxycarbonyl-3-oxo-3-phenylpropyl)-L-alanine (substrate) in the solution are shown in Table 2. 50% (w/w) water-containing 5% Pd—C (4.0 g) was added and the catalytic reduction was carried out in hydrogen atmosphere (atmospheric pressure) under the conditions of the inner temperature of 20° C. and an agitation power of a range from 0.5 to 1 kW/m$^3$. While the reaction was monitored with HPLC, the reaction was stopped when the formation rate of N-(1-ethoxycarbonyl-3-phenylpropyl)-L-alanine was about 80%. The formation rate (%) of N-(1-ethoxycarbonyl-3-phenylpropyl)-L-alanine, and the amount (% (w/w)) of N-(1-ethoxycarbonyl-3-cyclohexylpropyl)-L-alanine (cyclohexyl form) as a by-product based on N-(1-ethoxycarbonyl-3-phenylpropyl)-L-alanine were examined. The result are shown in Table 2.

TABLE 2

| Amount of sulfuric acid | | Cyclohexyl form (% (w/w)) | Formation rate (%) |
|---|---|---|---|
| Concentration (N) | Equivalent | | |
| 0.5 | 3 | 0.1 | 84 |
| 1.0 | 6 | 0.1 | 85 |
| 1.5 | 4.5 | 0.1 | 84 |
| 1.7 | 10 | 0.1 | 81 |
| 2 | 6 | 0.1 | 83 |
| 2.6 | 16 | 0.1 | 75 |
| 3 | 4.5 | 0.1 | 83 |

According to the same manner as that described in Example 1, the separation from the resulting reaction solution was conducted. As a result, the effect of removing the cyclohexyl form by purification was not recognized.

Comparative Example 2

N-(1-ethoxycarbonyl-3-oxo-3-phenylpropyl)-L-alanine [(1S/1R)=9.0] (10.0 g, 34 mmoles) was added to a mixture of 7% (w/w) water-containing ethanol containing a predetermined amount of sulfuric acid. The concentration of sulfuric acid and the equivalent thereof based on N-(1-ethoxycarbonyl-3-oxo-3-phenylpropyl)-L-alanine (substrate) in the solution are shown in Table 3. 50% (w/w) water-containing 5% Pd—C (4.0 g) was added and the catalytic reduction was carried out in hydrogen atmosphere (atmosphere pressure) under the conditions of the inner temperature of 20° C. and an agitation power of a range from 0.5 to 1 kW/m$^3$. While the reaction was monitored with HPLC, the reaction was stopped when the formation rate of N-(1-ethoxycarbonyl-3-phenylpropyl)-L-alanine was about 80%. The formation rate (%) of N-(1-ethoxycarbonyl-3-phenylpropyl)-L-alanine, and the amount (% (w/w)) of N-(1-ethoxycarbonyl-3-cyclohexylpropyl)-L-alanine (cyclohexyl form) as a by-product based on N-(1-ethoxycarbonyl-3-phenylpropyl)-L-alanine were examined. The result are shown in Table 3.

TABLE 3

| Amount of sulfuric acid | | Cyclohexyl form (% (w/w)) | Formation rate (%) |
|---|---|---|---|
| Concentration (N) | Equivalent | | |
| 0.3 | 2 | 0.6 | 83 |
| 0.7 | 2 | 0.5 | 84 |
| 1.4 | 2 | 0.5 | 85 |
| 6.4 | 6 | 0.6 | 60 |

According to the same manner as that described in Example 1, the separation from the resulting reaction solution was conducted. As a result, the effect of removing the cyclohexyl form by purification was not recognized.

Example 10

According to the same manner as that described in Example 1, the catalytic reduction was carried out to give a reaction solution containing 10% (w/w) of N-(1(R)-ethoxycarbonyl-3-phenylpropyl)-L-alanine, 0.1% (w/w) of N-(1-ethoxycarbonyl-3-cyclohexylpropyl)-L-alanine and 7% (w/w) of N-(1-carboxy-3-phenylpropyl)-L-alanine, based on N-(1(S)-ethoxycarbonyl-3-phenylpropyl)-L-alanine, respectively. The reaction yield was 85%. According to the same manner as that described in Example 1, the crystallization from the reaction solution was carried out to give N-(1(S)-ethoxycarbonyl-3-phenylpropyl)-L-alanine (6.3 g, 23 mmoles). The yield from N-(1(S)-ethoxycarbonyl-3-oxo-3-phenylpropyl)-L-alanine: 75%, HPLC purity: 99.0% (w/w), the content of N-(1(R)-ethoxycarbonyl-3-phenylpropyl)-L-alanine: not detected, the content of N-(1-ethoxycarbonyl-3-cyclohexylpropyl)-L-alanine: 0.1% (w/w), the content of N-(1-carboxy-3-phenylpropyl)-L-alanine: 0.1% (w/w), residue on ignition: 0.1% (w/w).

Example 11

N-(1(S)-ethoxycarbonyl-3-phenylpropyl)-L-alanine (40.0 g) (purity: 95% (w/w), content of pure substance: 38.0 g) containing 3.0% (w/w) of N-(1(R)-ethoxycarbonyl-3-phenylpropyl)-L-alanine and 1.0% (w/w) of N-(1-carboxy-3-phenylpropyl)-L-alanine was added to 400 ml of water. With stirring, 15 ml of 35% (w/w) hydrochloric acid was added. To the resulting solution, 8.0 g of 50% (w/w) water-containing active carbon was added, followed by stirring for 30 minutes. The active carbon was removed by filtration under reduced pressure, and washed with 100 ml of water. After the resulting filtrate and wash liquid were mixed, the crystallization was carried out under stirring with adding an aqueous 30% (w/w) sodium hydroxide solution at the inner temperature of a range from 25° to 30° C. over 1 hour. As a result, deposition of a crystal was started at pH 1. Finally, the pH was adjusted to 4.7 and the solution was stirred at 25° C. for 1 hour. The crystal of N-(1(S)-ethoxycarbonyl-3-phenylpropyl)-L-alanine was filtered and washed with 80 ml of water. The resulting crystal was vacuum-dried (30 mmHg to 0.1 mmHg) at a range from 40° to 60° C. to give 33.8 g of N-(1(S)-ethoxycarbonyl-3-phenylpropyl)-L-alanine. The yield was 89%. HPLC purity: 99.5% (w/w), the content of N-(1(R)-ethoxycarbonyl-3-phenylpropyl)-L-alanine was 0.1% (w/w), the content of N-(1-carboxy-3-phenylpropyl)-L-alanine: less than 0.1% (w/w).

INDUSTRIAL APPLICABILITY

According to the present invention, it is possible to produce the 1-alkoxycarbonyl-3-phenylpropyl derivative (II) having good quality, which contains a very small amount of the 1-alkoxycarbonyl-3-cyclohexylpropyl derivative (cyclohexyl form) (III) and the 1-carboxy-3-phenylpropyl derivative (carboxy form) (IV), simply and efficiently, in good productivity.

What is claimed is:

1. A process for preparing a 1-alkoxycarbonyl-3-phenylpropyl derivative represented by the formula (II):

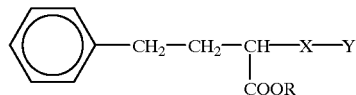

(II)

wherein R is an alkyl group, X is -Ala-, -Gly-, -Leu-, -Ile-, -Val-, -Orn-, -Lys- or -Hly-, in which ω-amino groups of -Orn-, -Lys- and -Hly- are protected with an acyl protecting group, Y is hydroxyl group, which comprises catalytically reducing a 1-alkoxycarbonyl-3-oxo-3-phenylpropyl derivative represented by the formula (I):

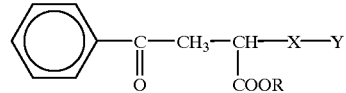

(I)

wherein R, X and Y are the same as defined above; the above-mentioned catalytic reduction being carried out in an alcohol or a solvent containing the alcohol in the presence of a strong acid having a concentration of 0.4 to 5 N, the amount of the strong acid being at least 3 equivalents based on one equivalent of the 1-alkoxycarbonyl-3-oxo-3-phenylpropyl derivative (1 mole) to control formation of a 1-alkoxycarbonyl-3-cyclohexylpropyl derivative represented by the formula (III):

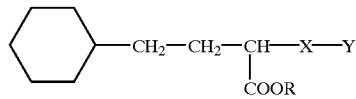

(III)

wherein R, X and Y are the same as defined above.

2. A process as claimed in claim 1 comprising separating the 1-alkoxycarbonyl-3-phenylpropyl derivative represented by the formula (II) from a reaction solution obtained by catalytic reduction, wherein a 1-carboxy-3-phenylpropyl derivative represented by the formula (IV):

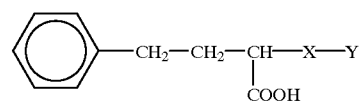

(IV)

wherein X and Y are the same as defined in claim 1, as a by-product, is removed.

3. A process as claimed in claim 2 wherein the strong acid is neutralized to pH 4.6±1.5.

4. A process as claimed in claim 1, 2 or 3 wherein X is -L-Ala-.

5. A process as claimed in claim 1, 2 or 3 wherein X is -L-Lys-, the ω-amino group of which is protected with an acyl protecting group.

6. A process as claimed in claim 2 wherein the separation of the 1-alkoxycarbonyl-3-phenylpropyl derivative represented by the formula (II) is carried out by crystallization from the aqueous solution.

7. A process as claimed in claim 6 wherein crystallization is carried out at temperatures not less than 30° C.

8. A process as claimed in claim 1, 2, or 3 wherein a Michael addition reaction mixture which contains the 1-alkoxycarbonyl-3-oxo-3-phenylpropyl derivative represented by the formula (I) obtained by Michael addition reaction of a β-benzoyl acrylate and an amino acid or a derivative thereof is used for catalytic reduction.

9. A process as claimed in claim 1, 2 or 3 wherein an alcohol, the water content of which is at most 50% (w/w), is used as a reaction solvent.

10. A process as claimed in claim 9 wherein an alcohol, the water content of which is within a range from 2 to 30% (w/w), is used as a reaction solvent.

11. A process as claimed in claim 1, 2, or 3 wherein sulfuric acid is used as a strong acid.

12. A process as claimed in claim 1, 2, or 3 wherein said strong acid is used in a concentration within a range from 3 to 15 equivalents based on 1 mole of the 1-alkoxycarbonyl-3-oxo-3-phenylpropyl derivative represented by the formula (I) as a 1 equivalent.

13. A process as claimed in claim 1, 2, or 3 wherein a palladium catalyst is used as a reduction catalyst.

14. A process as claimed in claim 13 wherein Pd—C, Pd-alumina or Pd-zeolite is used as a reduction catalyst.

15. A process as claimed in claim 1, 2, or 3 wherein a reaction temperature of catalytic reduction is within a range from 10° to 35° C.

16. A process as claimed in claim 1, 2, 3 wherein a pressure of hydrogen in said catalytic reduction is within a range from atmospheric pressure to 2 kg/cm$^2$G.

17. A process as claimed in claim 1, 2 or 3 wherein said catalytic reduction reaction is stopped before an intermediate represented by the formula:

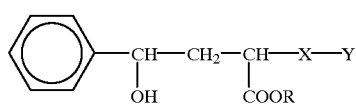

wherein R is an alkyl group, X is -Ala-, -Gly-, -Leu-, -Ile-, -Val-, -Orn-, -Lys- or -Hly-, in which the ω-amino groups of -Orn-, -Lys- and -Hly- are protected with an acyl protecting group, and Y is a hydroxyl group disappears.

18. A process for obtaining an N-(1(S)-ethoxycarbonyl-3-phenylpropyl)-L-alanine which is characterized by crystallizing N-(1(S)-ethoxycarbonyl-3-phenylpropyl)-L- alanine in the presence of at least one of N-(1-carboxy-3-phenylpropyl)-L-alanine and (N-(1(R)-ethoxycarbonyl-3-phenylpropyl)-L-alanine in an aqueous solution to give N-(1(S)-ethoxycarbonyl-3-phenylpropyl)-L-alanine and to remove N-(1-carboxy-3-phenylpropyl)-L-alanine and (N-(1 (R)-ethoxycarbonyl-3-phenylpropyl)-L-alanine.

19. A process as claimed in claim 18 wherein a pH value of said aqueous solution is pH 4.6±1.5.

20. A process as claimed in claim 1, wherein said catalytic reduction is carried out in the presence of a strong acid having a concentration of 0.5 to 3 N.

21. A process for obtaining an N-(1(S)-ethoxycarbonyl-3-phenylpropyl)-L-alanine according to claim 1 comprising crystallizing N-(1(S)-ethoxycarbonyl-3-phenylpropyl)-L-alanine with which at least one of N-(1-carboxy-3-phenylpropyl)-L-alanine and (N-(1(R)-ethoxycarbonyl-3-phenylpropyl)-L-alanine coexist in an aqueous solution to give N-(1(S)-ethoxycarbonyl-3-phenylpropyl)-L-alanine and to remove N-(1-carboxy-3-phenylpropyl)-L-alanine and N-(1(R)-ethoxycarbonyl-3-phenylpropyl)-L-alanine.

22. A process as claimed in claim 21 wherein a pH value of said aqueous solution is pH 4.6±1.5.

* * * * *